(12) United States Patent
Djupesland et al.

(10) Patent No.: US 8,899,229 B2
(45) Date of Patent: Dec. 2, 2014

(54) POWDER DELIVERY DEVICES

(75) Inventors: Per Gisle Djupesland, Oslo (NO);
Roderick Peter Hafner, Swindon (GB);
Colin David Sheldrake, Oxfordshire (GB)

(73) Assignee: OptiNose AS, Oslo (NO)

( * ) Notice: Subject to any disclaimer, the term of this patent is extended or adjusted under 35 U.S.C. 154(b) by 1704 days.

(21) Appl. No.: 11/816,984

(22) PCT Filed: Feb. 23, 2006

(86) PCT No.: PCT/GB2006/000631
§ 371 (c)(1),
(2), (4) Date: Jun. 10, 2009

(87) PCT Pub. No.: WO2006/090149
PCT Pub. Date: Aug. 31, 2006

(65) Prior Publication Data
US 2009/0293873 A1   Dec. 3, 2009

(30) Foreign Application Priority Data
Feb. 23, 2005 (GB) .................. 0503738.7

(51) Int. Cl.
*A61M 15/08* (2006.01)
*A61M 15/00* (2006.01)
*A61M 16/12* (2006.01)
*A61M 16/10* (2006.01)
*A61M 16/00* (2006.01)

(52) U.S. Cl.
CPC ........... *A61M 15/0028* (2013.01); *A61M 15/08* (2013.01); *A61M 15/0035* (2014.02); *A61M 15/0041* (2014.02); *A61M 15/0098* (2014.02); *A61M 16/127* (2014.02); *A61M 16/1075* (2013.01); *A61M 2016/0021* (2013.01); *A61M 2016/0027* (2013.01); *A61M 2202/064* (2013.01); *A61M 2205/07* (2013.01); *A61M 2205/3606* (2013.01); *A61M 2205/3673* (2013.01); *A61M 2205/8218* (2013.01); *A61M 2206/14* (2013.01); *A61M 2210/0618* (2013.01); *A61M 2210/0625* (2013.01)
USPC ............. 128/203.15; 128/203.16; 128/203.18

(58) Field of Classification Search
USPC ................ 128/203.1–203.15, 203.16–203.18
See application file for complete search history.

(56) References Cited

U.S. PATENT DOCUMENTS 4,013,075 A   3/1977   Cocozza
4,240,418 A *  12/1980   Rosskamp et al. ........ 128/203.15

(Continued)

FOREIGN PATENT DOCUMENTS

CA   2448425   12/2010
DE   19835346   2/2000

(Continued)

OTHER PUBLICATIONS

U.S. Appl. No. 13/603,108, Djupesland.

(Continued)

*Primary Examiner* — Stephen Crow
(74) *Attorney, Agent, or Firm* — Lihua Zheng; Mary Consalvi; Proskauer Rose LLP

(57) ABSTRACT

A nasal delivery device for delivering substance to a nasal cavity of a subject, the delivery device comprising: a substance supply unit for supplying a dose of substance to be delivered to the nasal cavity of the subject, the substance supply unit including an inlet and an outlet; a nosepiece unit including a nosepiece for fitting to a nasal cavity of the subject and being in fluid communication with the outlet of the substance supply unit; and a mouthpiece unit including a mouthpiece in fluid communication with the inlet of the substance supply unit and through which the subject in use exhales such as to entrain substance from the container chamber and deliver the same through the nosepiece, and at least one temperature modifier for reducing a temperature of the exhaled air flow such as to reduce the absolute humidity thereof.

42 Claims, 8 Drawing Sheets

(56) References Cited

U.S. PATENT DOCUMENTS

Figure 1:
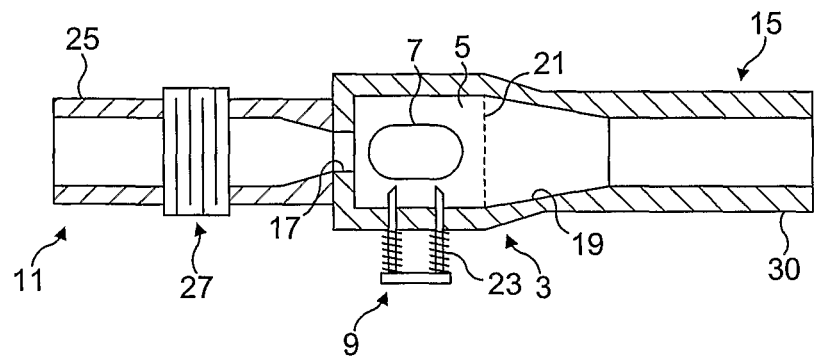
Figure 2:
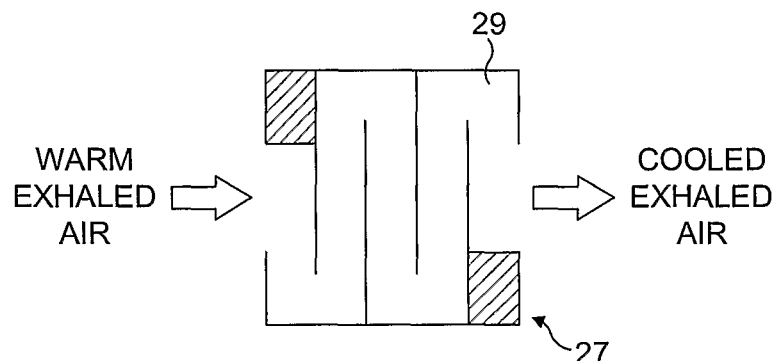
Figure 3:
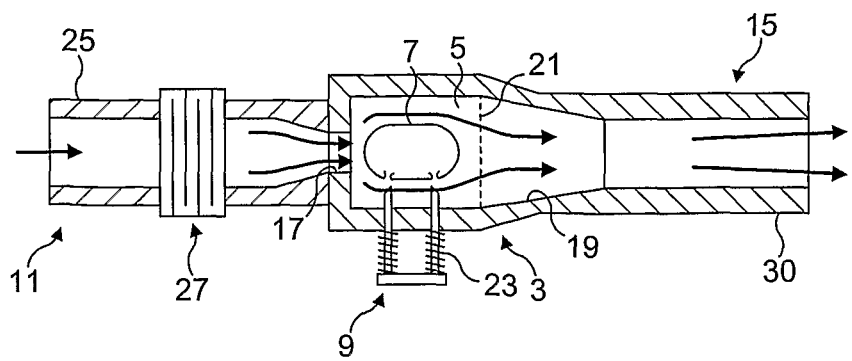
Figure 4:
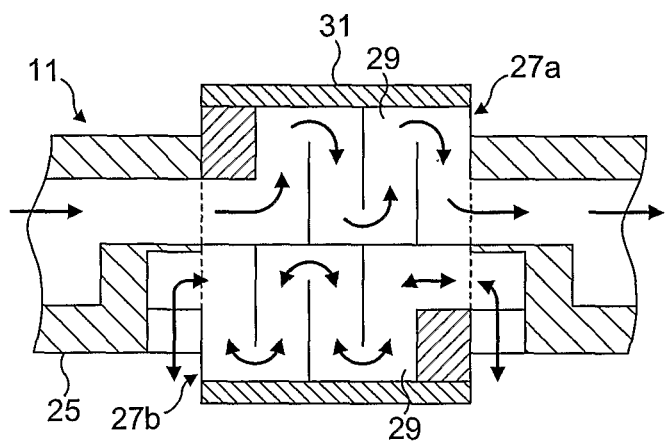
Figure 5:
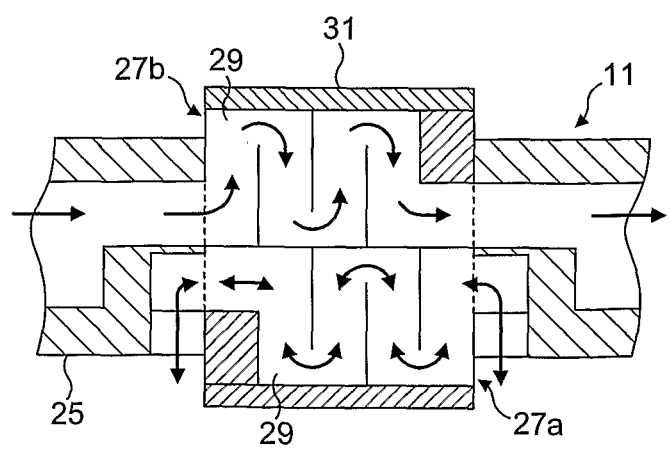
Figure 6:
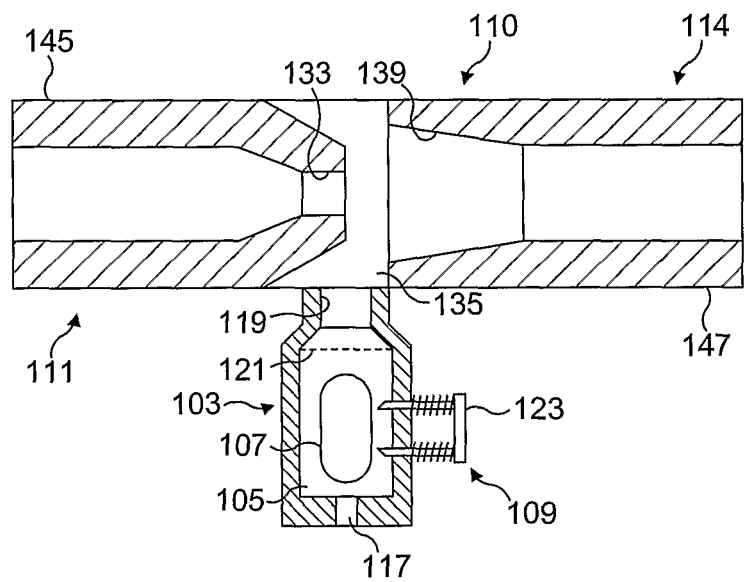

| | | | |
|---|---|---|---|
| 4,570,630 A * | 2/1986 | Elliott et al. | 128/203.15 |
| 4,819,625 A * | 4/1989 | Howe | 128/200.18 |
| 4,829,997 A * | 5/1989 | Douwens et al. | 128/201.13 |
| 4,889,114 A | 12/1989 | Kladders | |
| 5,239,993 A | 8/1993 | Evans | |
| 5,337,740 A | 8/1994 | Armstrong | |
| 5,373,841 A | 12/1994 | Kyllonen et al. | |
| 6,308,703 B1 * | 10/2001 | Alving et al. | 128/203.12 |
| 6,715,485 B1 | 4/2004 | Djupesland | |
| 7,347,201 B2 | 3/2008 | Djupesland | |
| 7,377,901 B2 | 5/2008 | Djupesland et al. | |
| 7,481,218 B2 | 1/2009 | Djupesland | |
| 7,543,581 B2 | 6/2009 | Djupesland | |
| 7,740,014 B2 | 6/2010 | Djupesland | |
| 7,784,460 B2 | 8/2010 | Djupesland et al. | |
| 7,841,337 B2 | 11/2010 | Djupesland | |
| 7,854,227 B2 | 12/2010 | Djupesland | |
| 7,934,503 B2 | 5/2011 | Djupesland | |
| 7,975,690 B2 | 7/2011 | Djupesland | |
| 8,047,202 B2 | 11/2011 | Djupesland | |
| 8,146,589 B2 | 4/2012 | Djupesland | |
| 8,171,929 B2 * | 5/2012 | Djupesland et al. | 128/200.23 |
| 8,327,844 B2 | 12/2012 | Djupesland | |
| 8,511,303 B2 | 8/2013 | Djupesland | |
| 8,522,778 B2 | 9/2013 | Djupesland | |
| 8,550,073 B2 | 10/2013 | Djupesland | |
| 8,555,877 B2 | 10/2013 | Djupesland | |
| 8,555,878 B2 | 10/2013 | Djupesland | |
| 2004/0043064 A1 | 3/2004 | Iorio et al. | |
| 2004/0112379 A1 | 6/2004 | Djupesland | |
| 2005/0056280 A1 | 3/2005 | Alston | |
| 2006/0219240 A1 | 10/2006 | Djupesland | |
| 2006/0219241 A1 | 10/2006 | Djupesland | |
| 2006/0225732 A1 | 10/2006 | Djupesland | |
| 2006/0231094 A1 | 10/2006 | Djupesland | |
| 2006/0254583 A1 * | 11/2006 | Deboeck et al. | 128/203.15 |
| 2007/0039614 A1 | 2/2007 | Djupesland | |
| 2007/0125371 A1 | 6/2007 | Djupesland | |
| 2008/0163874 A1 | 7/2008 | Djupesland | |
| 2008/0221471 A1 | 9/2008 | Djupesland | |
| 2008/0223363 A1 | 9/2008 | Djupesland | |
| 2008/0289629 A1 | 11/2008 | Djupesland | |
| 2009/0137621 A1 * | 5/2009 | Hochrainer et al. | 514/291 |
| 2009/0304802 A1 | 12/2009 | Djupesland | |
| 2009/0320832 A1 | 12/2009 | Djupestand | |
| 2010/0021535 A1 * | 1/2010 | Mizutani et al. | 424/451 |
| 2010/0035805 A1 | 2/2010 | Hafner | |
| 2010/0057047 A1 | 3/2010 | Djupesland | |
| 2010/0242959 A1 | 9/2010 | Djupesland | |
| 2010/0282246 A1 | 11/2010 | Djupesland et al. | |
| 2010/0288275 A1 * | 11/2010 | Djupesland et al. | 128/203.15 |
| 2010/0300439 A1 | 12/2010 | Djupesland et al. | |
| 2011/0023869 A1 | 2/2011 | Djupesland | |
| 2011/0053827 A1 | 3/2011 | Hafner | |
| 2011/0088690 A1 | 4/2011 | Djupesland | |
| 2011/0114087 A1 | 5/2011 | Djupesland | |
| 2011/0126830 A1 | 6/2011 | Djupesland | |
| 2011/0259329 A1 | 10/2011 | Djupesland | |
| 2011/0318345 A1 | 12/2011 | Djupesland | |
| 2012/0000459 A1 | 1/2012 | Djupesland | |
| 2012/0006323 A1 | 1/2012 | Djupesland | |
| 2012/0073571 A1 | 3/2012 | Djupesland | |
| 2012/0090608 A1 | 4/2012 | Djupesland | |
| 2012/0138050 A1 * | 6/2012 | Wondka et al. | 128/200.16 |
| 2012/0260915 A1 | 10/2012 | Djupesland | |
| 2013/0098362 A1 | 4/2013 | Djupesland | |
| 2013/0125889 A1 | 5/2013 | Djupesland | |

FOREIGN PATENT DOCUMENTS

| | | |
|---|---|---|
| DE | 10300982 | 7/2004 |
| EP | 0525720 | 12/1996 |
| EP | 0606486 | 8/2001 |
| EP | 1407795 | 8/2007 |
| GB | 2404867 | 2/2005 |
| GB | 2405350 | 3/2005 |
| GB | 2418147 | 3/2006 |
| JP | 53/0848741 | 7/1978 |
| JP | 54/053674 | 4/1979 |
| JP | 56/114801 | 2/1981 |
| JP | 63/248422 | 10/1988 |
| JP | 07/147255 | 6/1995 |
| JP | 08/238318 | 9/1996 |
| WO | 98/053869 | 12/1998 |
| WO | WO-00/51672 | 9/2000 |
| WO | 02/068031 | 9/2002 |
| WO | 03/009832 | 2/2003 |
| WO | 03/055547 | 6/2003 |
| WO | 03084591 | 10/2003 |
| WO | WO-03/090812 | 11/2003 |
| WO | WO-2004/060433 | 7/2004 |
| WO | WO-2004/082750 | 9/2004 |
| WO | WO-2004/091705 | 10/2004 |
| WO | WO-2004/103447 | 12/2004 |
| WO | WO-2005/021059 | 3/2005 |
| WO | WO-2006/030210 | 3/2006 |

OTHER PUBLICATIONS

U.S. Appl. No. 13/665,330, Djupesland.
U.S. Appl. No. 13/724,560, Djupesland.
U.S. Appl. No. 14/724,636, Djupesland.
U.S. Appl. No. 13/785,694, Djupesland.
U.S. Appl. No. 13/823,071, Djupesland.
U.S. Appl. No. 13/005,363, Hafner.
U.S. Appl. No. 14/047,390, Djupesland.
U.S. Appl. No. 14/058,647, Djupesland.

* cited by examiner

POWDER DELIVERY DEVICES

The present invention relates to a powder delivery device for the delivery of a powdered substance, in particular to the nasal airway, and both a powdered substance and a capsule for use with the same.

BACKGROUND OF THE INVENTION

There is an increasing interest in the nasal delivery of substances, typically pharmaceutical drugs, both as powders and liquids, for topical and systemic delivery.

Current delivery systems are not suited to the delivery of substances to the upper posterior region of the nasal airway, in particular targeted delivery to the olfactory region and the sinus ostia.

U.S. Pat. Nos. 4,013,075 and 4,889,114 disclose examples of prior art inhalation devices, which provide for the inhalation of a powdered substance from a capsule.

WO-A-00/051672, the content of which is herein incorporated by reference, discloses a delivery device for delivering a substance, in particular a medicament, in a bi-directional flow through the nasal cavities, that is, an air flow which passes into one nostril, around the posterior margin of the nasal septum and in the opposite direction out of the other nostril. A particular feature of this bi-directional mode of delivery is the ability to target defined regions in the nasal airway, for both topical and systemic delivery, in particular the upper posterior region which cannot be targeted with existing systems.

The present inventors have recognized that the delivery of powdered substances using the exhalation breath of a subject still presents a significant challenge, owing to the interaction of the moist exhaled air flow with the powdered substance prior to delivery into the nasal airway.

Exhalation into a device leads to condensation on the surfaces of the exposed device components, where the components are at a significantly lower temperature than the exhaled air flow, and significant condensation in the delivery channel will affect the consistency of the delivered doses.

SUMMARY OF THE INVENTION

It is an aim of the present invention to provide a delivery device which allows for the delivery of powdered substances, either supplied in capsules or blisters, which contain a pre-metered dose of substance with the appropriate particle size distribution and surface properties, or metered from bulk, where using the exhalation breath of the subject.

In one aspect the present invention provides a nasal delivery device which utilizes an exhalation breath to deliver a powdered substance, and includes a temperature modifier to reduce the absolute humidity of the exhaled air flow prior to entrainment of the powdered substance.

In another aspect the present invention provides a nasal delivery device which utilizes an exhalation breath to deliver a powdered substance, and incorporates a Venturi unit to draw a powdered substance into the exhaled air flow using an air flow of the ambient atmosphere.

In a further aspect the present invention provides a nasal delivery device which utilizes drive means, such as a pressurized gas supply or a turbine, to entrain a powdered substance into a substance gas flow, which in one embodiment is then entrained by an exhaled air flow.

In a yet further aspect the present invention provides a capsule which is formed from a lightweight material, such as a thin-wall section polymeric material, which reduces the energy required to move the capsule, typically by one or both of vibration and rotation, and thereby provides for emptying at reduced flow rates. In one embodiment the material has a reduced tendency to become tacky in the presence of moisture.

In a still further aspect the present invention provides a powder formulation which is formulated to have reduced hygroscopicity, and preferably a transiently-increased dissolution time, such as achieved by coating or blending, such as to reduce any loss of powdered substance in a device due to interaction with water condensate.

In one preferred aspect the present invention provides a nasal delivery device for delivering substance to a nasal cavity of a subject, the delivery device comprising: a substance supply unit for supplying a dose of substance to be delivered to the nasal cavity of the subject, the substance supply unit including an inlet and an outlet; a nosepiece unit including a nosepiece for fitting to a nasal cavity of the subject and being in fluid communication with the outlet of the substance supply unit; and a mouthpiece unit including a mouthpiece in fluid communication with the inlet of the substance supply unit and through which the subject in use exhales such as to entrain substance from the substance supply unit and deliver the same through the nosepiece, and at least one temperature modifier for reducing a temperature of the exhaled air flow such as to reduce the absolute humidity thereof.

In one embodiment the at least one temperature modifier comprises at least one elongate channel.

Preferably, the at least one temperature modifier comprises a plurality of elongate channels.

In one embodiment the mouthpiece unit includes a plurality of temperature modifiers which can be fluidly connected successively to the mouthpiece, and a switching mechanism which allows for one of the temperature modifiers to be fluidly connected to the mouthpiece.

Preferably, when the one of the temperature modifiers is fluidly connected to the mouthpiece, the at least one other temperature modifier is vented to atmosphere.

In one embodiment the switching mechanism comprises a rotatable member to which the temperature modifiers are disposed, whereby rotation of the switching mechanism provides for the one of the temperature modifiers to be in fluid communication with the mouthpiece.

Preferably, the substance supply unit comprises a container chamber for receiving a substance-containing container which contains a dose of substance.

In one embodiment the container chamber is substantially cylindrical in shape.

In another embodiment the container chamber is substantially spherical in shape.

In one embodiment the container chamber and the nosepiece comprise a unitary, replaceable component.

In one embodiment the substance supply unit comprises a rupturing mechanism for rupturing the container as contained in the container chamber.

In one embodiment the container is formed of a material which exhibits insufficient tackiness, and preferably substantially no surface tackiness, in the presence of moisture such as not to adhere to an inner surface of the container chamber during emptying of the container.

Preferably, the container is formed of a material which exhibits insufficient tackiness in the presence of moisture in the exhalation air flow for a period of up to about 5 s following exhalation.

More preferably, the container is formed of a material which exhibits insufficient tackiness in the presence of moisture in the exhalation air flow for a period of up to about 2 s following exhalation.

Still more preferably, the container is formed of a material which exhibits insufficient tackiness in the presence of moisture in the exhalation air flow for a period of up to about 1 s following exhalation.

In one embodiment the container is formed substantially of a cellulose derivative.

Preferably, the container is formed substantially of one of hydroxypropyl methylcellulose (HPMC), hydroxypropylcellulose, methylcellulose, ethylcellulose and carboxymethylcellulose.

In another embodiment the container is formed substantially of gelatine.

In a further embodiment the container is formed of a plastics material.

In a still further embodiment the container includes a coating of a material which exhibits insufficient tackiness in the presence of moisture such as not to adhere to an inner surface of the container chamber during emptying of the container.

Preferably, the coating is formed of a material which exhibits insufficient tackiness in the presence of moisture in the exhalation air flow for a period of up to about 5 s following exhalation.

More preferably, the coating is formed of a material which exhibits insufficient tackiness in the presence of moisture in the exhalation air flow for a period of up to about 2 s following exhalation.

Still more preferably, the coating is formed of a material which exhibits insufficient tackiness in the presence of moisture in the exhalation air flow for a period of up to about 1 s following exhalation.

Preferably, the coating comprises substantially one of parylene, hydroxypropyl methylcellulose (HPMC), hydroxypropylcellulose, methylcellulose, ethylcellulose, carboxymethylcellulose, polyvinyl alcohol, acrylic acid polymer, methacrylic acid polymer, ethyl acrylic acid polymer, cellulose acetate phthalate, polyvinyl acetate phthalate, hydroxypropyl methylcellulose phthalate and hydroxyl methylcellulose acetate succinate, or any combination of layers thereof.

In one embodiment the container comprises a body of gelatine.

In one embodiment the container comprises a capsule.

In one embodiment the capsule is substantially cylindrical in shape.

In another embodiment the capsule is substantially spherical in shape.

In one embodiment the at least one temperature modifier is configured to reduce the temperature of the exhaled air flow by more than about 5° C.

Preferably, the at least one temperature modifier is configured to reduce the temperature of the exhaled air flow by at least about 12° C.

Preferably, the at least one temperature modifier is configured to allow a flow therethrough at a flow rate of at least about 10 l/min at a pressure of less than about 2 kPa, and preferably less than about 1 kPa.

More preferably, the at least one temperature modifier is configured to allow a flow therethrough at a flow rate of at least about 20 l/min at a pressure of less than about 2 kPa, and preferably less than about 1 kPa.

Still more preferably, the at least one temperature modifier is configured to allow a flow therethrough at a flow rate of at least about 30 l/min at a pressure of less than about 2 kPa, and preferably less than about 1 kPa.

Yet more preferably, the at least one temperature modifier is configured to allow a flow therethrough at a flow rate of at least about 40 l/min at a pressure of less than about 2 kPa, and preferably less than about 1 kPa.

Still yet more preferably, the at least one temperature modifier is configured to allow a flow therethrough at a flow rate of at least about 50 l/min at a pressure of less than about 2 kPa, and preferably less than about 1 kPa.

Preferably, the at least one temperature modifier is configured such as to provide a pressure drop of not more than about 0.5 kPa to the exhaled air flow.

More preferably, the at least one temperature modifier is configured such as to provide a pressure drop of not more than about 0.25 kPa to the exhaled air flow.

Still more preferably, the at least one temperature modifier is configured such as to provide a pressure drop of not more than about 0.10 kPa to the exhaled air flow.

Yet more preferably, the at least one temperature modifier is configured such as to provide a pressure drop of not more than about 0.05 kPa to the exhaled air flow.

Still yet more preferably, the at least one temperature modifier is configured such as to provide a pressure drop of not more than about 0.025 kPa to the exhaled air flow.

In another embodiment the at least one temperature modifier comprises a thermoelectric device.

In another preferred aspect the present invention provides a nasal delivery device for delivering substance to a nasal cavity of a subject, the delivery device comprising: a substance supply unit for supplying a dose of substance to be delivered to the nasal cavity of the subject, the substance supply unit comprising a substance-receiving chamber including an inlet and an outlet, and a Venturi unit for drawing a flow of ambient air through the substance-receiving chamber; a nosepiece unit including a nosepiece for fitting to the nasal cavity of the subject and being in fluid communication with the Venturi unit; and a mouthpiece unit including a mouthpiece in fluid communication with the Venturi unit and through which the subject in use exhales such as to entrain substance from the substance-receiving chamber and deliver the same through the nosepiece.

Preferably, the substance-receiving chamber comprises a container chamber for receiving a substance-containing container which contains a dose of substance.

In one embodiment the container chamber is substantially cylindrical in shape.

In another embodiment the container chamber is substantially spherical in shape.

In one embodiment the container chamber and the nosepiece comprise a unitary, replaceable component.

In one embodiment the substance supply unit comprises a rupturing mechanism for rupturing the substance-containing container as contained in the container chamber.

In one embodiment the container is formed of a material which exhibits insufficient tackiness, and preferably substantially no surface tackiness, in the presence of moisture such as not to adhere to an inner surface of the container chamber during emptying of the container.

Preferably, the container is formed of a material which exhibits insufficient tackiness in the presence of moisture in the exhalation air flow for a period of up to about 5 s following exhalation.

More preferably, the container is formed of a material which exhibits insufficient tackiness in the presence of moisture in the exhalation air flow for a period of up to about 2 s following exhalation.

Still more preferably, the container is formed of a material which exhibits insufficient tackiness in the presence of moisture in the exhalation air flow for a period of up to about 1 s following exhalation.

In one embodiment the container is formed substantially of a cellulose derivative.

Preferably, the container is formed substantially of one of hydroxypropyl methylcellulose (HPMC), hydroxypropylcellulose, methylcellulose, ethylcellulose and carboxymethylcellulose.

In another embodiment the container is formed substantially of gelatine.

In a further embodiment the container is formed of a plastics material.

In a still further embodiment the container includes a coating of a material which exhibits insufficient tackiness in the presence of moisture such as not to adhere to an inner surface of the container chamber during emptying of the container.

Preferably, the coating is formed of a material which exhibits insufficient tackiness in the presence of moisture in the exhalation air flow for a period of up to about 5 s following exhalation.

More preferably, the coating is formed of a material which exhibits insufficient tackiness in the presence of moisture in the exhalation air flow for a period of up to about 2 s following exhalation.

Still more preferably, the coating is formed of a material which exhibits insufficient tackiness in the presence of moisture in the exhalation air flow for a period of up to about 1 s following exhalation.

Preferably, the coating comprises substantially one of parylene, hydroxypropyl methylcellulose (HPMC), hydroxypropylcellulose, methylcellulose, ethylcellulose, carboxymethylcellulose, polyvinyl alcohol, acrylic acid polymer, methacrylic acid polymer, ethyl acrylic acid polymer, cellulose acetate phthalate, polyvinyl acetate phthalate, hydroxypropyl methylcellulose phthalate and hydroxyl methylcellulose acetate succinate, or any combination of layers thereof.

In one embodiment the container comprises a body of gelatine.

In one embodiment the container comprises a capsule.

In one embodiment the capsule is substantially cylindrical in shape.

In another embodiment the capsule is substantially spherical in shape.

In one embodiment the Venturi unit comprises a first, driving air flow inlet which is in fluid communication with the mouthpiece unit and provides a constriction which acts to accelerate the exhaled air flow to deliver a driving air flow at a higher velocity, a second, substance air flow inlet which is in fluid communication with the substance supply unit and through which is in use drawn a substance air flow from the substance-receiving chamber which entrains substance as contained therein, and an air flow outlet which is in fluid communication with the nosepiece unit and through which the driving air flow and the substance air flow are in use delivered.

In one embodiment the driving air flow is directed substantially perpendicularly to the substance air flow.

In another embodiment the driving air flow is directed substantially parallel to the substance air flow.

In one embodiment the mouthpiece unit is fluidly connected to the substance supply unit, such as to provide a supplemental air flow to the substance-receiving chamber on exhalation by the subject into the mouthpiece unit.

Preferably, the mouthpiece unit includes a flow channel which is fluidly connected to the inlet of the substance-receiving chamber.

In a further preferred aspect the present invention provides a nasal delivery device for delivering substance to a nasal cavity of a subject, the delivery device comprising: a substance supply unit for supplying a dose of substance to be delivered to the nasal cavity of the subject, the substance supply unit comprising a substance-receiving chamber including an inlet and an outlet, and a gas supply unit for delivering a gas flow through the substance-receiving chamber such as in use to provide a gas flow entraining substance from the outlet of the substance-receiving chamber; a nosepiece unit including a nosepiece for fitting to the nasal cavity of the subject and being in fluid communication with the outlet of the substance-receiving chamber; and a mouthpiece unit including a mouthpiece in fluid communication with the outlet of the substance-receiving chamber and the nosepiece and through which the subject in use exhales such as to entrain substance as delivered from the substance-receiving chamber and deliver the same through the nosepiece.

Preferably, the substance-receiving chamber comprises a container chamber for receiving a substance-containing container which contains a dose of substance.

In one embodiment the container chamber is substantially cylindrical in shape.

In another embodiment the container chamber is substantially spherical in shape.

In one embodiment the container chamber and the nosepiece comprise a unitary, replaceable component.

In one embodiment the substance supply unit comprises a rupturing mechanism for rupturing the container as contained in the container chamber.

In one embodiment the container is formed of a material which exhibits insufficient tackiness, and preferably substantially no surface tackiness, in the presence of moisture such as not to adhere to an inner surface of the container chamber during emptying of the container.

Preferably, the container is formed of a material which exhibits insufficient tackiness in the presence of moisture in the exhalation air flow for a period of up to about 5 s following exhalation.

More preferably, the container is formed of a material which exhibits insufficient tackiness in the presence of moisture in the exhalation air flow for a period of up to about 2 s following exhalation.

Still more preferably, the container is formed of a material which exhibits insufficient tackiness in the presence of moisture in the exhalation air flow for a period of up to about 1 s following exhalation.

In one embodiment the container is formed substantially of a cellulose derivative.

Preferably, the container is formed substantially of one of hydroxypropyl methylcellulose (HPMC), hydroxypropylcellulose, methylcellulose, ethylcellulose and carboxymethylcellulose.

In another embodiment the container is formed substantially of gelatine.

In a further embodiment the container is formed of a plastics material.

In a still further embodiment the container includes a coating of a material which exhibits insufficient tackiness in the presence of moisture such as not to adhere to an inner surface of the container chamber during emptying of the container.

Preferably, the coating is formed of a material which exhibits insufficient tackiness in the presence of moisture in the exhalation air flow for a period of up to about 5 s following exhalation.

More preferably, the coating is formed of a material which exhibits insufficient tackiness in the presence of moisture in the exhalation air flow for a period of up to about 2 s following exhalation.

Still more preferably, the coating is formed of a material which exhibits insufficient tackiness in the presence of moisture in the exhalation air flow for a period of up to about 1 s following exhalation.

Preferably, the coating comprises substantially one of parylene, hydroxypropyl methylcellulose (HPMC), hydroxypropylcellulose, methylcellulose, ethylcellulose, carboxymethylcellulose, polyvinyl alcohol, acrylic acid polymer, methacrylic acid polymer, ethyl acrylic acid polymer, cellulose acetate phthalate, polyvinyl acetate phthalate, hydroxypropyl methylcellulose phthalate and hydroxyl methylcellulose acetate succinate, or any combination of layers thereof.

In one embodiment the container comprises a body formed substantially of gelatine.

In one embodiment the container comprises a capsule.

In one embodiment the capsule is substantially cylindrical in shape.

In another embodiment the capsule is substantially spherical in shape.

In one embodiment the gas supply unit comprises a volume of pressurized gas which, when released, provides the entraining gas flow.

In another embodiment the gas supply unit comprises a charged turbine which, when released, provides the entraining gas flow.

In one embodiment the gas supply unit is a breath-actuated unit.

In one embodiment the gas supply unit is actuated in response to generation of a predeterminable flow rate through the mouthpiece unit.

In another embodiment the gas supply unit is actuated in response to generation of a predeterminable pressure at the mouthpiece unit.

In another embodiment the gas supply unit is a manually-actuated unit.

In a still further preferred aspect the present invention provides a capsule for containing a powdered substance which exhibits insufficient tackiness, and preferably no surface tackiness, in the presence of moisture such as not to adhere to an inner surface of a capsule chamber which contains the capsule during emptying of the capsule.

Preferably, the capsule is formed of a material which exhibits insufficient tackiness in the presence of moisture in an exhalation air flow for a period of up to about 5 s.

More preferably, the capsule is formed of a material which exhibits insufficient tackiness in the presence of moisture in the exhalation air flow for a period of up to about 2 s.

Still more preferably, the capsule is formed of a material which exhibits insufficient tackiness in the presence of moisture in the exhalation air flow for a period of up to about 1 s.

In one embodiment the capsule is formed substantially of a cellulose derivative.

Preferably, the capsule is formed substantially of one of hydroxypropyl methylcellulose (HPMC), hydroxypropylcellulose, methylcellulose, ethylcellulose and carboxymethylcellulose.

In another embodiment the capsule is formed of a plastics material.

In one embodiment the capsule includes a coating of a material which exhibits insufficient tackiness in the presence of moisture such as not to adhere to an inner surface of the capsule chamber during emptying of the capsule.

Preferably, the coating is formed of a material which exhibits insufficient tackiness in the presence of moisture in an exhalation air flow for a period of up to about 5 s.

More preferably, the coating is formed of a material which exhibits insufficient tackiness in the presence of moisture in the exhalation air flow for a period of up to about 2 s.

Still more preferably, the coating is formed of a material which exhibits insufficient tackiness in the presence of moisture in the exhalation air flow for a period of up to about 1 s.

Preferably, the coating comprises substantially one of parylene, hydroxypropyl methylcellulose (HPMC), hydroxypropylcellulose, methylcellulose, ethylcellulose, carboxymethylcellulose, polyvinyl alcohol, acrylic acid polymer, methacrylic acid polymer, ethyl acrylic acid polymer, cellulose acetate phthalate, polyvinyl acetate phthalate, hydroxypropyl methylcellulose phthalate and hydroxyl methylcellulose acetate succinate, or any combination of layers thereof.

In one embodiment the capsule comprises a body formed substantially of gelatine.

In one embodiment the capsule is substantially cylindrical in shape.

In another embodiment the capsule is substantially spherical in shape.

In one embodiment the capsule comprises a body of thin-wall section.

Preferably, the body has a thickness of not more than about 0.25 mm.

More preferably, the body has a thickness of not more than about 0.20 mm.

In a yet further preferred aspect the present invention extends to the use of a capsule, containing a powdered substance, which exhibits insufficient tackiness, and preferably no surface tackiness, in the presence of moisture such as not to adhere to an inner surface of a capsule chamber which contains the same during emptying of the capsule in an exhaled air flow.

Preferably, the capsule is formed of a material which exhibits insufficient tackiness in the presence of moisture in an exhalation air flow for a period of up to about 5 s.

More preferably, the capsule is formed of a material which exhibits insufficient tackiness in the presence of moisture in the exhalation air flow for a period of up to about 2 s.

Still more preferably, the capsule is formed of a material which exhibits insufficient tackiness in the presence of moisture in the exhalation air flow for a period of up to about 1 s.

In one embodiment the capsule is formed substantially of a cellulose derivative.

Preferably, the capsule is formed substantially of one of hydroxypropyl methylcellulose (HPMC), hydroxypropylcellulose, methylcellulose, ethylcellulose and carboxymethylcellulose.

In another embodiment the capsule is formed of a plastics material.

In one embodiment the capsule includes a coating of a material which exhibits insufficient tackiness in the presence of moisture such as not to adhere to an inner surface of the capsule chamber during emptying of the capsule.

Preferably, the coating is formed of a material which exhibits insufficient tackiness in the presence of moisture in an exhalation air flow for a period of up to about 5 s.

More preferably, the coating is formed of a material which exhibits insufficient tackiness in the presence of moisture in the exhalation air flow for a period of up to about 2 s.

Still more preferably, the coating is formed of a material which exhibits insufficient tackiness in the presence of moisture in the exhalation air flow for a period of up to about 1 s.

Preferably, the coating comprises substantially one of parylene, hydroxypropyl methylcellulose (HPMC), hydroxypropylcellulose, methylcellulose, ethylcellulose, carboxymethylcellulose, polyvinyl alcohol, acrylic acid polymer, methacrylic acid polymer, ethyl acrylic acid polymer, cellulose acetate phthalate, polyvinyl acetate phthalate, hydroxypropyl methylcellulose phthalate and hydroxyl methylcellulose acetate succinate, or any combination of layers thereof.

In one embodiment the capsule comprises a body formed substantially of gelatine.

In one embodiment the capsule is substantially cylindrical in shape.

In another embodiment the capsule is substantially spherical in shape.

In one embodiment the capsule comprises a body of thin-wall section.

Preferably, the body has a thickness of not more than about 0.25 mm.

More preferably, the body has a thickness of not more than about 0.20 mm.

In yet another preferred aspect the present invention provides a nasal delivery device for delivering substance to a nasal cavity of a subject, the delivery device comprising: a substance supply unit for supplying a dose of substance to be delivered to the nasal cavity of the subject, the substance supply unit including an inlet and an outlet; a nosepiece unit including a nosepiece for fitting to a nasal cavity of the subject and being in fluid communication with the outlet of the substance supply unit; and a mouthpiece unit including a mouthpiece in fluid communication with the inlet of the substance supply unit and through which the subject in use exhales such as to entrain substance from the substance supply unit and deliver the same through the nosepiece.

In still another preferred aspect the present invention provides a method of delivering substance to a nasal cavity of a subject, the method comprising the steps of: supplying a dose of substance to be delivered to the nasal cavity of the subject; fitting a nosepiece unit including a nosepiece to the nasal cavity of the subject; and the subject exhaling through a mouthpiece unit such as to entrain the supplied dose of substance and deliver the same through the nosepiece to the nasal cavity of the subject, wherein the mouthpiece unit includes at least one temperature modifier for reducing a temperature of the exhaled air flow such as to reduce the absolute humidity thereof.

In yet still another preferred aspect the present invention provides a method of delivering substance to a nasal cavity of a subject, the method comprising the steps of: providing a dose of substance to be delivered to the nasal cavity of the subject in a substance-receiving chamber; fitting a nosepiece unit including a nosepiece to the nasal cavity of the subject; providing a Venturi unit which is operative to draw a flow of ambient air through the substance-receiving chamber; and the subject delivering an exhaled air flow to the Venturi unit such as to draw a flow of ambient air through the substance-receiving chamber, which entrains the powdered substance therein, and to the nosepiece such as to deliver the exhaled air flow entraining the powdered substance to the nasal cavity of the subject.

In a yet still further preferred aspect the present invention provides a method of delivering substance to a nasal cavity of a subject, the method comprising the steps of: providing a dose of substance to be delivered to the nasal cavity of the subject in a substance-receiving chamber; fitting a nosepiece unit including a nosepiece to the nasal cavity of the subject; providing a gas flow of ambient air through the substance-receiving chamber, which entrains the powdered substance therein; and the subject delivering an exhaled air flow to the nosepiece which entrains the gas flow entraining the powdered substance, such as to deliver the powdered substance to the nasal cavity of the subject.

BRIEF DESCRIPTION OF THE DRAWINGS

Preferred embodiments of the present invention will now be described hereinbelow by way of example only with reference to the accompanying drawings, in which:

FIG. 1 illustrates a delivery device in accordance with a first embodiment of the present invention;

FIG. 2 illustrates the heat exchanger of the delivery device of FIG. 1;

FIG. 3 illustrates the delivery device of FIG. 1, in the operative state;

FIG. 4 illustrates the mouthpiece unit of a delivery device as a modification of the delivery device of FIG. 1, in a first operative configuration;

FIG. 5 illustrates the mouthpiece unit of FIG. 4, in a second operative configuration;

FIG. 6 illustrates a delivery device in accordance with a second embodiment of the present invention;

FIG. 7 illustrates the delivery device of FIG. 6, in the operative state;

FIG. 8 illustrates a delivery device as a modification of the delivery device of FIG. 6;

FIG. 9 illustrates the delivery device of FIG. 8, in the operative state;

FIG. 10 illustrates a delivery device in accordance with a third embodiment of the present invention;

FIG. 11 illustrates the delivery device of FIG. 10, in the operative state;

FIG. 12 illustrates a delivery device in accordance with a fourth embodiment of the present invention;

FIG. 13 illustrates the delivery device of FIG. 12, in a first operative state;

FIG. 14 illustrates the delivery device of FIG. 12, in a second operative state;

FIG. 15 illustrates a delivery device as one modification of the delivery device of FIG. 12;

FIG. 16 illustrates a delivery device as one modification of the delivery device of FIG. 1; and FIG. 17 illustrates a delivery device as another modification of the delivery device of FIG. 1.

FIGS. 1 to 3 illustrate a delivery device in accordance with a first embodiment of the present invention.

DETAILED DESCRIPTION OF THE INVENTION

The delivery device comprises a substance supply unit 3 which includes a chamber 5 which receives a capsule 7, which contains a metered amount of a powdered substance which is to be delivered by the delivery device, a rupturing mechanism 9 for rupturing the capsule 7, a mouthpiece unit 11 which is in fluid communication with the chamber 5 and is gripped in use in the mouth of a subject, and a nosepiece unit 15 which is in fluid communication with the chamber 5 and is fitted to one nostril of the subject. For ease of illustration, the delivery device is illustrated in an elongate configuration, but, in its practical embodiment, the mouthpiece unit 11 and the nosepiece unit 15 are configured for fitting to the mouth and one nostril of the subject.

The substance supply unit 3 includes an inlet 17 which fluidly connects the chamber 5 thereof with the mouthpiece unit 11 and an outlet 19 which fluidly connects the chamber 5 thereof with the nosepiece unit 15.

In this embodiment the substance supply unit 3 includes a grid 21, here a gauze, which is disposed at the outlet 19 thereof and acts to prevent the capsule 7 or parts thereof from escaping from the chamber 5.

In this embodiment the chamber 5 is cylindrical in shape.

In another embodiment the chamber 5 can be substantially spherical in shape, which is particularly advantageous in allowing for the release of the powdered substance from the capsule 7 in any operative position.

In this embodiment the chamber 5 and the grid 21, as components which contact the capsule 7 and the contained powder, are fabricated from a material having a low moisture sensitivity, here a plastics material, such as to reduce any tendency to become tacky in the presence of moisture, and therefore reduce the tendency for the capsule 7 and the powdered substance as contained thereby to adhere to the wall of the chamber 5 or the grid 21.

In this embodiment the rupturing mechanism 9 comprises a piercing element 23, here including two pins, which is operable to pierce the capsule 7, and thereby provide for the release of the contained powdered substance on the generation of a flow through the chamber 5.

The mouthpiece unit 11 comprises a mouthpiece 25, in this embodiment as defined by a tubular section, which is gripped in the mouth of the subject, and a heat exchanger 27 which is in fluid communication with the mouthpiece 25 and acts to draw heat from the exhaled air flow as delivered through the mouthpiece 25, thus decreasing the temperature of the air flow as delivered to the chamber 5. By decreasing the temperature of the air flow, the humidity of the air flow is reduced, with the water vapor condensing in the heat exchanger 27, and the impact of condensation is significantly reduced, thus allowing for successive doses of powdered substance to be delivered without affecting the release of powdered substance from the capsules 7.

As illustrated in FIG. 2, in this embodiment the heat exchanger 27 comprises a channel 29 which has a zig-zag, serpentine configuration, with a circular cross section. In other embodiments the channel 29 could have other configurations, for example, a rectangular cross section.

In this embodiment the channel 29 has an effective length of 200 mm and an effective diameter of 4 mm, which reduces the temperature of an exhaled air flow which has a flow rate of 30 l/min to about 25° C. from about 37° C., where the channel 29 is at a temperature of 20° C.

The reduction in temperature is calculated as follows:

$$T_e=T_w-(T_w-T_i)e^{-hAmC}$$

Where: $T_e$ is the fluid temperature at the exit of the channel 29;

$T_w$ is the fluid temperature at the wall of the channel 29;

$T_i$ is the fluid temperature at the inlet of the channel 29;

h is the heat transfer coefficient between the gas flowing through the channel 29 and the material of the channel 29;

A is the surface area of the channel 29;

m is the mass flow rate; and

C is the specific heat capacity of the gas flowing through the channel 29.

This calculation assumes turbulent flow in the channel 29 ($Nu=0.023Re^{0.8}Pr^{0.3}$).

In other embodiments the channel 29 can include features to enhance the heat transfer coefficient from the exhaled air flow to the wall of the channel 29, such that the effective length of the channel 29 can be considerably reduced. Typical features include nodules or areas of relative surface roughness that create turbulence and so enhance the heat transfer.

In other embodiments the heat exchanger 27 could comprise a plurality of channels 29.

In one embodiment the heat exchanger 27 comprises four channels 29, as parallel ducts, which each have a width of 10 mm, a height of 1.5 mm and a length of 60 mm. This configuration reduces the temperature of an exhaled air flow which has a flow rate of 30 l/min by about 5° C., where the channels 29 are at a temperature of 20° C., and also cause only a very small pressure drop of 0.024 kPa.

The nosepiece unit 15 comprises a nosepiece 30, in this embodiment as defined by a tubular section, which is inserted into a nostril of the subject, in this embodiment to provide a sealing fit therewith.

In this embodiment the nosepiece 30, as a component which contacts the powdered substance, is fabricated from a material having a low moisture sensitivity, here a plastics material, such as to reduce any tendency to become tacky in the presence of moisture, and therefore reduce the tendency for the powdered substance to adhere to the wall of the nosepiece 30.

In one embodiment the capsule 7 is a gelatine capsule.

In another embodiment the capsule 7 can be manufactured from a material which has a reduced tendency to become tacky in the presence of moisture, as occurs with gelatine capsules, and therefore reduce the tendency for the capsule 7 to adhere to the wall of the chamber 5 or the grid 21.

In one embodiment the capsule 7 is formed of a cellulose derivative, such as hydroxypropyl methylcellulose (HPMC), hydroxypropylcellulose, methylcellulose, ethylcellulose and carboxymethylcellulose In another embodiment the capsule 7 can comprise a plastics material, preferably a water insoluble material, such as a polycarbonate.

In one embodiment the capsule 7 can be manufactured from a lightweight material, such as thin-wall section polymeric materials, which reduces the energy required to move the capsule 7, typically by one or both of vibration and rotation, and thereby allow the delivery device to be operated at reduced flow rates, which is particularly advantageous for nasal delivery.

In one embodiment the capsule 7 has a wall section of less than about 0.25 mm, and more preferably less than about 0.2 mm.

In an alternative embodiment the capsule 7 can include an outer coating of a material which has a reduced tendency to become tacky in the presence of moisture, as occurs with gelatine capsules, and therefore reduce the tendency for the capsule 7 to adhere to the wall of the chamber 5 or the grid 21.

In one embodiment the coated capsule 7 can be formed of gelatine.

In one embodiment the coating can comprise one of parylene, hydroxypropyl methylcellulose (HPMC), hydroxypropylcellulose, methylcellulose, ethylcellulose, carboxymethylcellulose, polyvinyl alcohol, acrylic acid polymer, methacrylic acid polymer, ethyl acrylic acid polymer, cellulose acetate phthalate, polyvinyl acetate phthalate, hydroxypropyl methylcellulose phthalate and hydroxyl methylcellulose acetate succinate.

The delivery device of this embodiment is operative to discharge the powdered substance from the capsule 7 by rotation and vibration of the capsule 7, and thus the capsule 7 is preferably formed of a material or coated with a material which exhibits substantially no tackiness in the presence of a moist environment, here a saturated exhaled air flow, that is, does not exhibit an increased moisture content at the outer surface thereof, which would prevent reliable rotation and vibration of the capsule 7.

In this embodiment, as illustrated in FIG. 1, the capsule 7 is cylindrical in shape with hemispherical ends.

In other embodiments the capsule 7 could have other geometric forms, such as spherical, which allows for efficient powder release at low flow rates.

In one embodiment the capsule 7 can comprise two or more parts.

In one alternative embodiment the capsule 7 can be constructed to act as the primary environmental barrier for the powdered substance. For example, the capsule 7 could be constructed from a relatively thick-walled cylindrical section of a polymeric material which includes two metalized thin film closure members which act to seal the ends of the cylindrical section and thus enclose the same.

In one embodiment, where the delivery device is a reusable device, the chamber 5, which contains the capsule 7, and the nosepiece 30 comprise a unitary, replaceable component.

In operation, as illustrated in FIG. 3, a subject operates the rupturing mechanism 9 to rupture the capsule 7, inserts the nosepiece 30 into one of his/her nostrils, grips the mouthpiece 25 in his/her mouth, and exhales through the mouthpiece 25.

The exhaled air flow is reduced in temperature by the heat exchanger 27 on delivery therethrough, such as to reduce the absolute humidity of the exhaled air flow, and this cooled air is then driven through the chamber 5, which acts to move the capsule 7, in this embodiment by vibration and rotation, and entrain the powdered substance as contained by the capsule 7.

The exhaled air flow, as then entraining the powdered substance, is delivered though the nosepiece 30 into one nasal cavity of the subject.

In this embodiment the exhaled air flow has such a pressure as to pass around the posterior region of the nasal septum, and into the other nasal cavity, thereby achieving a bi-directional air flow as described in the applicants' earlier WO-A-00/051672.

In one modification, as illustrated in FIGS. 4 and 5, the mouthpiece unit 11 includes a plurality of, in this embodiment first and second heat exchangers 27*a, b* which can be used successively, such as to allow for the evaporation of the condensed moisture from the one or more previously-used heat exchangers 27*a, b*, and a switching mechanism 31 which allows for one of the heat exchangers 27*a, b* to be fluidly connected to the mouthpiece 25.

In this embodiment the switching mechanism 31 comprises a rotatable member to which the heat exchangers 27*a, b* are disposed, whereby rotation of the switching mechanism 31 provides for one of the heat exchangers 27*a, b* to be in fluid communication with the mouthpiece 25 and the at least one other of the heat exchangers 27*a, b* to be in fluid communication with the atmosphere. FIG. 4 illustrates a first configuration, in which the first heat exchanger 27*a* is in fluid communication with the mouthpiece 25 and the second heat exchanger 27*b* is vented to atmosphere. FIG. 5 illustrates a second configuration, in which the second heat exchanger 27*b* is in fluid communication with the mouthpiece 25 and the first heat exchanger 27*a* is vented to atmosphere.

With this configuration, the one of the heat exchangers 27*a, b* which is in fluid communication with the mouthpiece 25 acts to cool the exhaled air flow as delivered therethrough, and thereby trap water vapor from the exhaled air, and the other of the heat exchangers 27*a, b* which is vented to atmosphere provides for evaporation of the water condensate as trapped from a previous exhalation therethrough.

In an alternative embodiment the switching mechanism 31 could be operatively coupled to the rupturing mechanism 9, such as to provide for operation of the switching mechanism 31 with each operation of the rupturing mechanism 9.

FIGS. 6 and 7 illustrate a nasal delivery device in accordance with a second embodiment of the present invention.

The delivery device comprises a substance supply unit 103 which includes a chamber 105 which receives a capsule 107, which contains a metered amount of a powdered substance which is to be delivered by the delivery device, a rupturing mechanism 109 for rupturing the capsule 107, a Venturi unit 110 which is in fluid communication with the chamber 105 and is operative to draw an air flow of the ambient atmosphere through the chamber 105, a mouthpiece unit 111 which is in fluid communication with the Venturi unit 110 and is gripped in use in the mouth of a subject, and a nosepiece unit 114 which is in fluid communication with the Venturi unit 110 and is fitted to one nostril of the subject. For ease of illustration, the delivery device is illustrated in an elongate configuration, but, in its practical embodiment, the mouthpiece unit 111 and the nosepiece unit 114 are configured for fitting to the mouth and one nostril of the subject.

The substance supply unit 103 includes an inlet 117 which fluidly connects the chamber 105 thereof with the ambient atmosphere and an outlet 119 which fluidly connects the chamber 105 thereof with the Venturi unit 110.

In this embodiment the substance supply unit 103 includes a grid 121, here a gauze, which is disposed at the outlet 119 thereof and acts to prevent the capsule 107 or parts thereof from escaping from the chamber 105.

In this embodiment the chamber 105 is cylindrical in shape.

In another embodiment the chamber 105 could be spherical in shape, which is particularly advantageous in allowing for the release of the powdered substance from the capsule 107 when in any operative position.

In this embodiment the chamber 105 and the grid 121, as components which contact the capsule 107 and the contained powdered substance, are fabricated from a material having a low moisture sensitivity, here a plastics material, such as to reduce any tendency to become tacky in the presence of moisture, and therefore reduce the tendency for the capsule 107 and the powdered substance as contained thereby to adhere to the wall of the chamber 105 or the grid 121.

In this embodiment the rupturing mechanism 109 comprises a piercing element 123, here including two pins, which is operable to pierce the capsule 107, and thereby provide for the release of the contained powdered substance on the generation of a flow through the chamber 105.

In one embodiment the capsule 107 is a gelatine capsule.

In another embodiment the capsule 107 can be manufactured from a material which has a reduced tendency to become tacky in the presence of moisture, as occurs with gelatine capsules, and therefore reduce the tendency for the capsule 107 to adhere to the wall of the chamber 105 or the grid 121.

In one embodiment the capsule 107 is formed of a cellulose derivative, such as hydroxypropyl methylcellulose (HPMC), hydroxypropylcellulose, methylcellulose, ethylcellulose and carboxymethylcellulose In another embodiment the capsule 107 can comprise a plastics material, preferably a water insoluble material, such as a polycarbonate.

In one embodiment the capsule 107 can be manufactured from a lightweight material, such as thin-wall section polymeric materials, which reduces the energy required to move the capsule 107, typically by one or both of vibration and rotation, and thereby allows the delivery device to be operated at reduced flow rates, which is particularly advantageous for nasal delivery.

In one embodiment the capsule 107 has a wall section of less than about 0.25 mm, and more preferably less than about 0.2 mm.

In an alternative embodiment the capsule 107 can include an outer coating of a material which has a reduced tendency to become tacky in the presence of moisture, as occurs with gelatine capsules, and therefore reduce the tendency for the capsule 107 to adhere to the wall of the chamber 105 or the grid 121.

In one embodiment the coated capsule 107 can be formed of gelatine.

In one embodiment the coating can comprise one of parylene, hydroxypropyl methylcellulose (HPMC), hydroxypropylcellulose, methylcellulose, ethylcellulose, carboxymethylcellulose, polyvinyl alcohol, acrylic acid polymer, methacrylic acid polymer, ethyl acrylic acid polymer, cellulose acetate phthalate, polyvinyl acetate phthalate, hydroxypropyl methylcellulose phthalate and hydroxyl methylcellulose acetate succinate, or any combination of layers thereof.

The delivery device of this embodiment is operative to discharge the powdered substance from the capsule 107 by rotation and vibration of the capsule 107, and thus the capsule 107 is preferably formed of a material or coated with a material which exhibits substantially no tackiness in the presence of a moist environment, here a saturated exhaled air flow, that is, does not exhibit an increased moisture content at the outer surface thereof, which would prevent reliable rotation and vibration of the capsule 107.

In this embodiment the capsule 107 is cylindrical in shape, with hemispherical ends.

In other embodiments the capsule 107 could have other geometric forms, such as spherical, which allows for efficient powder release at low flow rates.

In one embodiment the capsule 107 can comprise two or more parts.

In one alternative embodiment the capsule 107 can be constructed to act as the primary environmental barrier for the powdered substance. For example, the capsule 107 could be constructed from a relatively thick-walled cylindrical section of a polymeric material which includes two metalized thin film closure members which act to seal the ends of the cylindrical section and thus enclose the same.

The Venturi unit 110 comprises a first, driving air flow inlet 133 which is in fluid communication with the mouthpiece unit 111 and provides a constriction which acts to accelerate the exhaled air flow to deliver a driving air flow at a higher velocity, a second, substance air flow inlet 135 which is in fluid communication with the outlet 119 of the substance supply unit 103 and through which, by the reduced local pressure as developed thereat by the Venturi effect, is drawn a substance air flow from the chamber 105 of the substance supply unit 103 which entrains the powdered substance, and an air flow outlet 139 which is in fluid communication with the nosepiece unit 114 and through which the driving air flow and the substance air flow are delivered. In this embodiment the driving air flow is directed substantially perpendicularly to the substance air flow.

This configuration, which utilizes ambient air to entrain the powdered substance from the capsule 107, is particularly advantageous, in avoiding the use of exhaled air to entrain the powdered substance. Exhaled air has a high humidity which would lead to condensation both in the chamber 105 and the capsule 107, which can cause problems in the complete entrainment of the powdered substance, both in terms of adhesion of the capsule 107 to the wall of the chamber 105 and adhesion of the powdered substance to the wall of the capsule 107, particularly where the powdered substance is a hygroscopic powder.

The mouthpiece unit 111 comprises a mouthpiece 145, in this embodiment as defined by a tubular section, which is gripped in the mouth of the subject.

The nosepiece unit 114 comprises a nosepiece 147, in this embodiment as defined by a tubular section, which is inserted into a nostril of the subject, in this embodiment to provide a sealing fit therewith.

In this embodiment the nosepiece 147, as a component which contacts the powdered substance, is fabricated from a material having a low moisture sensitivity, here a plastics material, such as to reduce any tendency to become tacky in the presence of moisture, and therefore reduce the tendency for the powdered substance to adhere to the wall of the nosepiece 147.

In one embodiment, where the delivery device is a re-usable device, the chamber 105, which contains the capsule 107, and the nosepiece 147 comprise a unitary, replaceable component.

Figure 7:
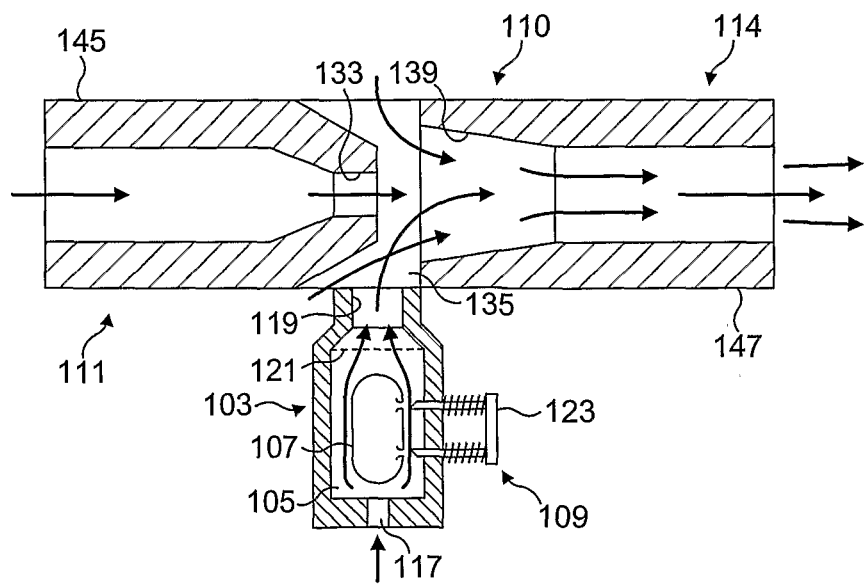

In operation, as illustrated in FIG. 7, a subject operates the rupturing mechanism 109 to rupture the capsule 107, inserts the nosepiece 147 into one of his/her nostrils, grips the mouthpiece 145 in his/her mouth, and exhales through the mouthpiece 145.

The exhaled air flow is forced through the driving air flow inlet 133 of the Venturi unit 110, which acts to deliver the exhaled air flow as a driving air flow over the substance air flow inlet 135 of the Venturi unit 110 and draw a substance air flow, which entrains powdered substance, from the chamber 105 of the substance supply unit 103. The substance air flow acts to move the capsule 107, in this embodiment by vibration and rotation, and entrain the powdered substance as contained by the capsule 107.

The exhaled air flow, as then entraining the powdered substance, passes through the air flow outlet 139 of the Venturi unit 110, and is delivered though the nosepiece 147 into one nasal cavity of the subject.

In this embodiment the exhaled air flow has such a pressure as to pass around the posterior margin of the nasal septum, and into the other nasal cavity, thereby achieving a bi-directional air flow as described in the applicants' earlier WO-A-00/051672.

Figure 8:
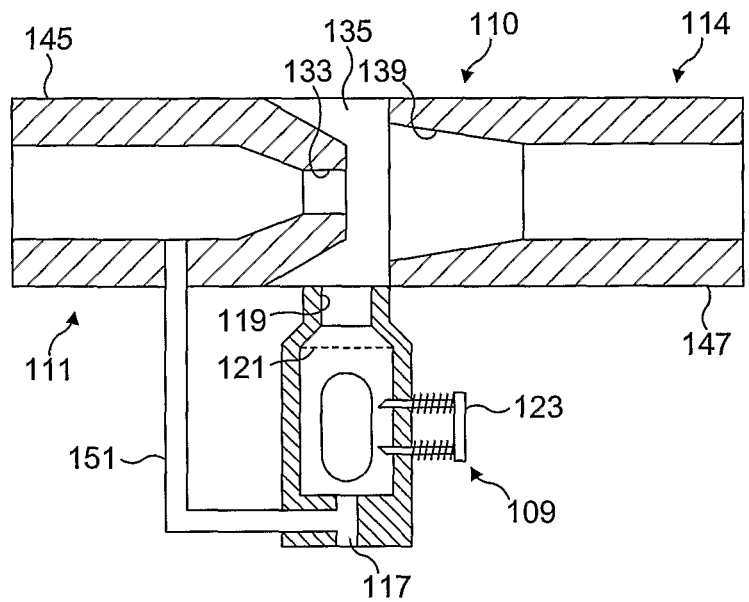
Figure 9:
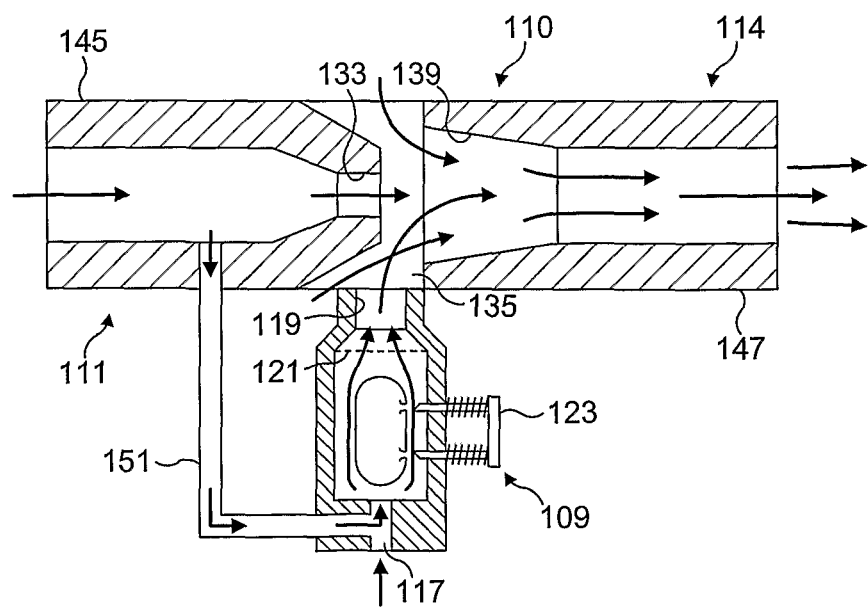

In one modification of the above-described delivery device, as illustrated in FIGS. 8 and 9, the substance supply unit 103 can be additionally fluidly connected to the mouthpiece unit 111, in this embodiment by a flow channel 151 which fluidly connects the mouthpiece 145 to the inlet 117 of the substance supply unit 103, such as to provide for a supplemental air flow to the chamber 105, which assists in entraining the powdered substance as contained by the capsule 107.

By regulating this supplementary air flow and blending the same with the ambient air as entrained through the inlet 117 of the substance supply unit 103, the resulting air flow still has a reduced absolute humidity (water vapour content) as compared with an exhaled air flow, where the ambient air is not saturated.

Operation of this device, which is illustrated in FIG. 9, is the same as for the delivery device of the above-described second embodiment.

Figure 10:
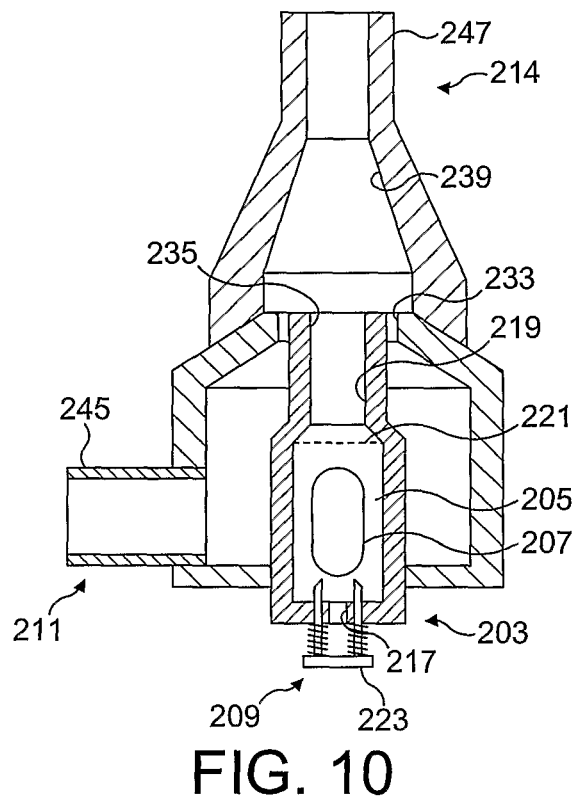
Figure 11:
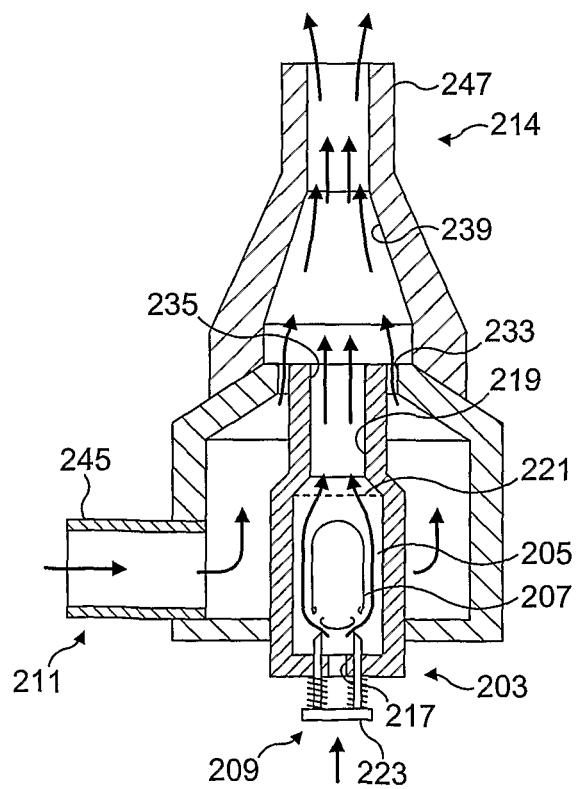
Figure 12:
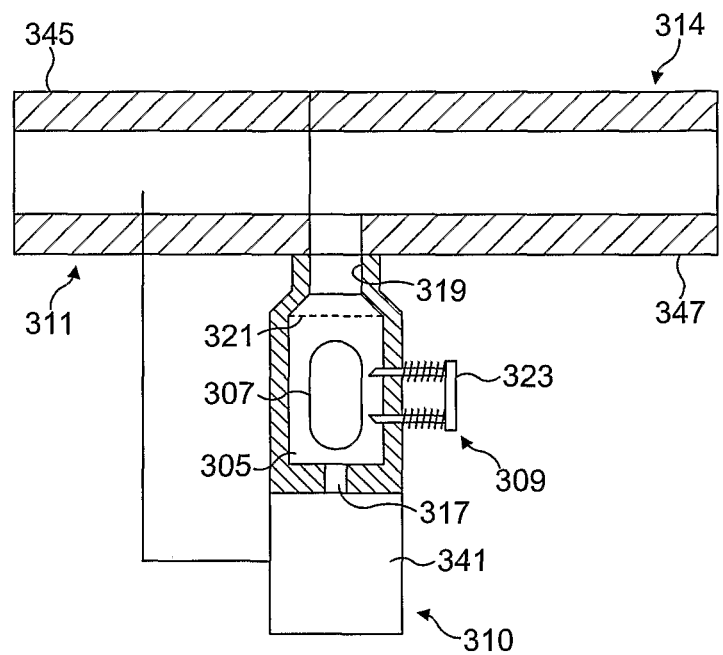
Figure 13:
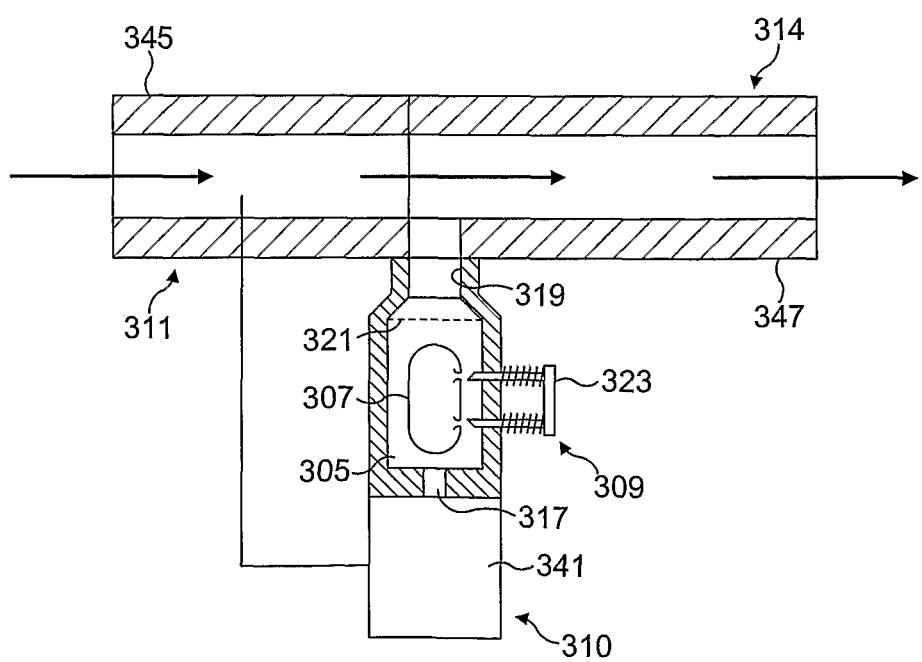
Figure 14:
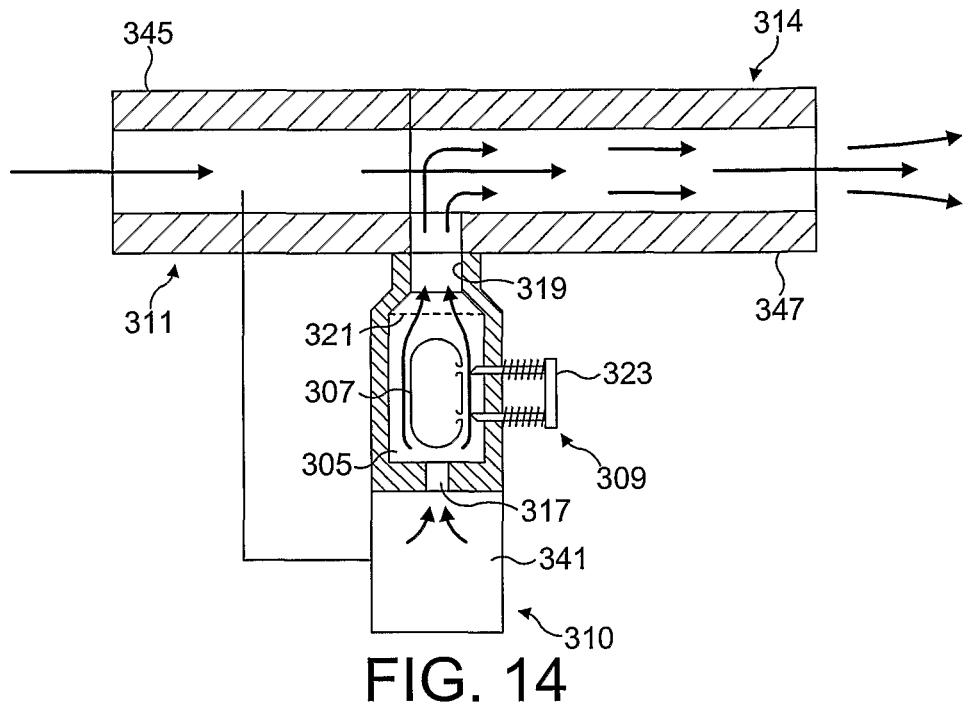
Figure 15:
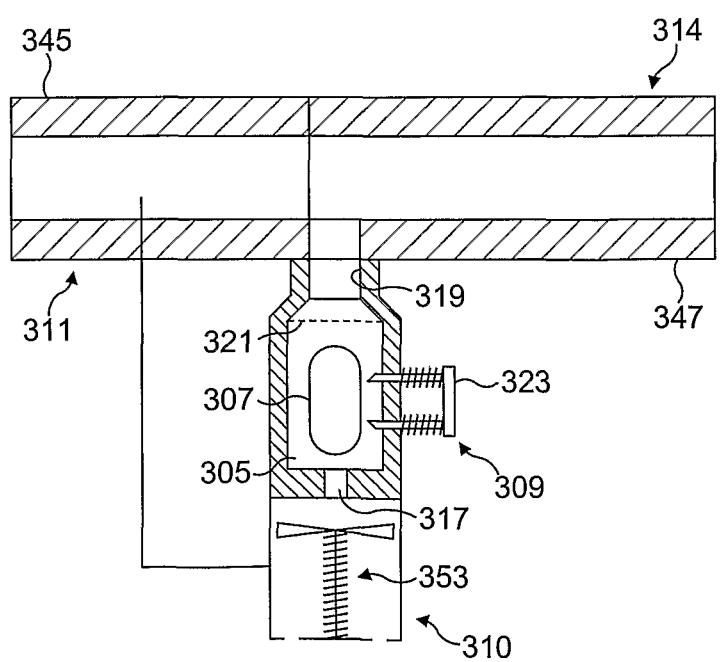
Figure 16:
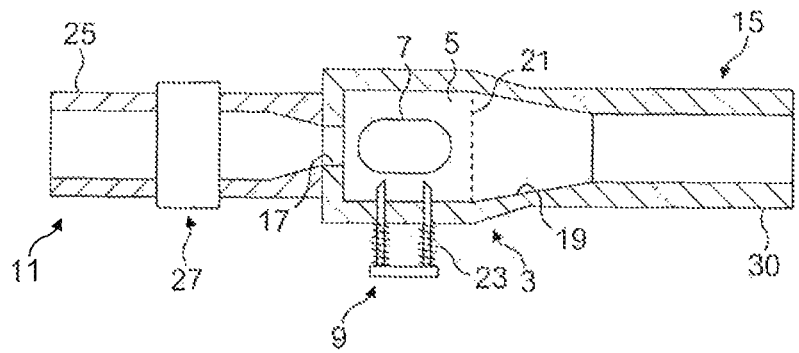

FIGS. 10 and 11 illustrate a nasal delivery device in accordance with a third embodiment of the present invention.

The delivery device comprises a substance supply unit 203 which includes a chamber 205 which receives a capsule 207, which contains a metered amount of a powdered substance which is to be delivered by the delivery device, a rupturing mechanism 209 for rupturing the capsule 207, a Venturi unit 210 which is operative to draw an air flow of the ambient atmosphere through the chamber 205, a mouthpiece unit 211 which is in fluid communication with the Venturi unit 210 and is gripped in use in the mouth of a subject, and a nosepiece unit 214 which is in fluid communication with the Venturi unit 210 and is fitted to one nostril of the subject. For ease of illustration, the delivery device is illustrated in an orthogonal configuration, but, in its practical embodiment, the mouthpiece unit 211 and the nosepiece unit 214 are configured for fitting to the mouth and one nostril of the subject.

The substance supply unit 203 includes an inlet 217 which fluidly connects the chamber 205 thereof with the ambient atmosphere and an outlet 219 which fluidly connects the chamber 205 thereof with the Venturi unit 210.

In this embodiment the substance supply unit 203 includes a grid 221, here a gauze, which is disposed at the outlet 219 thereof and acts to prevent the capsule 207 or parts thereof from escaping from the chamber 205.

In this embodiment the chamber 205 is cylindrical in shape.

In another embodiment the chamber 205 could be spherical in shape, which is particularly advantageous in allowing for the release of the powdered substance from the capsule 207 when in any operative position.

In this embodiment the chamber 205 and the grid 221, as components which contact the capsule 207 and the contained powdered substance, are fabricated from a material having a low moisture sensitivity, here a plastics material, such as to reduce any tendency to become tacky in the presence of moisture, and therefore reduce the tendency for the capsule 207 and the powdered substance as contained thereby to adhere to the wall of the chamber 205 or the grid 221.

In this embodiment the rupturing mechanism 209 comprises a piercing element 223, here including two pins, which is operable to pierce the capsule 207, and thereby provide for the release of the contained powdered substance on the generation of a flow through the chamber 205.

In one embodiment the capsule 207 is a gelatine capsule.

In another embodiment the capsule 207 can be manufactured from a material which has a reduced tendency to become tacky in the presence of moisture, as occurs with gelatine capsules, and therefore reduce the tendency for the capsule 207 to adhere to the wall of the chamber 205 or the grid 221.

In one embodiment the capsule 207 is formed of a cellulose derivative, such as hydroxypropyl methylcellulose (HPMC), hydroxypropylcellulose, methylcellulose, ethylcellulose and carboxymethylcellulose In another embodiment the capsule 207 can comprise a plastics material, preferably a water insoluble material, such as a polycarbonate.

In one embodiment the capsule 207 can be manufactured from a lightweight material, such as thin-wall section polymeric materials, which reduces the energy required to move the capsule 207, typically by one or both of vibration and rotation, and thereby allows the delivery device to be operated at reduced flow rates, which is particularly advantageous for nasal delivery.

In one embodiment the capsule 207 has a wall section of less than about 0.25 mm, and more preferably less than about 0.2 mm.

In an alternative embodiment the capsule 207 can include an outer coating of a material which has a reduced tendency to become tacky in the presence of moisture, as occurs with gelatine capsules, and therefore reduce the tendency for the capsule 207 to adhere to the wall of the chamber 205 or the grid 221.

In one embodiment the coated capsule 207 can be formed of gelatine.

In one embodiment the coating can comprise one of parylene, hydroxypropyl methylcellulose (HPMC), hydroxypropylcellulose, methylcellulose, ethylcellulose, carboxymethylcellulose, polyvinyl alcohol, acrylic acid polymer, methacrylic acid polymer, ethyl acrylic acid polymer, cellulose acetate phthalate, polyvinyl acetate phthalate, hydroxypropyl methylcellulose phthalate and hydroxyl methylcellulose acetate succinate, or any combination of layers thereof.

The delivery device of this embodiment is operative to discharge the powdered substance from the capsule 207 by rotation and vibration of the capsule 207, and thus the capsule 207 is preferably formed of a material or coated with a material which exhibits substantially no tackiness in the presence of a moist environment, here a saturated exhaled air flow, that is, does not exhibit an increased moisture content at the outer surface thereof, which would prevent reliable rotation and vibration of the capsule 207.

In this embodiment the capsule 207 is cylindrical in shape, with hemispherical ends.

In other embodiments the capsule 207 could have other geometric forms, such as spherical, which allows for efficient powder release at low flow rates.

In one embodiment the capsule 207 can comprise two or more parts.

In one alternative embodiment the capsule 207 can be constructed to act as the primary environmental barrier for the powdered substance. For instance, the capsule 207 could be constructed from a relatively thick-walled cylindrical section of a polymeric material which includes two metalized thin film closure members which act to seal the ends of the cylindrical section and thus enclose the same.

The Venturi unit 210 comprises at least one driving air flow inlet 233 which is in fluid communication with the mouthpiece unit 211 and provides a constriction which acts to accelerate the exhaled air flow to deliver at least one driving air flow at a higher velocity, a second, substance air flow inlet 235 which is fluid communication with the outlet 219 of the substance supply unit 203 and through which, by the reduced local pressure as developed thereat by the Venturi effect, is drawn a substance air flow from the chamber 205 of the substance supply unit 203 which entrains the powdered substance, and an air flow outlet 239 which is in fluid communication with the nosepiece unit 214 and through which the driving air flow and the substance air flow are delivered. In this embodiment the at least one driving air flow is directed substantially parallel to the substance air flow.

In this embodiment the Venturi unit 210 comprises a plurality of air flow inlets 233 which are disposed in an annular arrangement, here concentrically, about the substance air flow inlet 235.

This configuration, which utilizes ambient air to entrain the powdered substance from the capsule 207, is particularly advantageous, in avoiding the use of exhaled air to entrain the powdered substance. Exhaled air has a high humidity which would lead to condensation both in the chamber 205 and the capsule 207, which can cause problems in the complete entrainment of the powdered substance, both in terms of adhesion of the capsule 207 and the contained powdered substance to the wall of the chamber 205 and adhesion of the powdered substance to the capsule 207, particularly where the powdered substance is a hygroscopic powder.

The mouthpiece unit 211 comprises a mouthpiece 245, in this embodiment as defined by a tubular section, which is gripped in the mouth of the subject.

The nosepiece unit 214 comprises a nosepiece 247, in this embodiment as defined by a tubular section, which is inserted into a nostril of the subject, in this embodiment to provide a sealing fit therewith.

In this embodiment the nosepiece 247, as a component which contacts the powdered substance, is fabricated from a material having a low moisture sensitivity, here a plastics material, such as to reduce any tendency to become tacky in the presence of moisture, and therefore reduce the tendency for the powdered substance to adhere to the wall of the nosepiece 247.

In one embodiment, where the delivery device is a re-usable device, the chamber 205, which contains the capsule 207, and the nosepiece 247 comprise a unitary, replaceable component.

In operation, as illustrated in FIG. 11, a subject operates the rupturing mechanism 209 to rupture the capsule 207, inserts the nosepiece 247 into one of his/her nostrils, grips the mouthpiece 245 in his/her mouth, and exhales through the mouthpiece 245.

The exhaled air flow is forced through the at least one driving air flow inlet 233 of the Venturi unit 210, which acts to deliver the exhaled air flow as a driving air flow past the substance air flow inlet 235 of the Venturi unit 210 and draw a substance air flow, which entrains powdered substance, from the chamber 205 of the substance supply unit 203. The substance air flow acts to move the capsule 207, in this embodiment by vibration and rotation, and entrain the powdered substance as contained by the capsule 207.

The exhaled air flow, as then entraining the powdered substance, passes through the air flow outlet 239 of the Venturi unit 210, and is delivered though the nosepiece 247 into one nasal cavity of the subject.

In this embodiment the exhaled air flow has such a pressure as to pass around the posterior margin of the nasal septum, and into the other nasal cavity, thereby achieving a bi-directional air flow as described in the applicants' earlier WO-A-00/051672.

FIGS. 12 to 14 illustrate a nasal delivery device in accordance with a fourth embodiment of the present invention.

The delivery device comprises a substance supply unit 303 which includes a chamber 305 which receives a capsule 307, which contains a metered amount of a powdered substance which is to be delivered by the delivery device, a rupturing mechanism 309 for rupturing the capsule 307, a gas supply unit 310 which is operative to deliver a gas flow through the chamber 305, a mouthpiece unit 311 which is in fluid communication with the chamber 305 and is gripped in use in the mouth of a subject, and a nosepiece unit 314 which is in fluid communication with the chamber 305 and is fitted to one nostril of the subject. For ease of illustration, the delivery device is illustrated in an elongate configuration, but, in its practical embodiment, the mouthpiece unit 311 and the nosepiece unit 314 are configured for fitting to the mouth and one nostril of the subject.

The substance supply unit 303 includes an inlet 317 which fluidly connects the chamber 305 thereof with the gas supply unit 310 and an outlet 319 which fluidly connects the chamber 305 thereof with the mouthpiece unit 311 and the nosepiece unit 314.

In this embodiment the substance supply unit 303 includes a grid 321, here a gauze, which is disposed at the outlet 319 thereof and acts to prevent the capsule 307 or parts thereof from escaping from the chamber 305.

In this embodiment the chamber 305 is cylindrical in shape.

In another embodiment the chamber 305 could be spherical in shape, which is particularly advantageous in allowing for the release of the powdered substance from the capsule 307 when in any operative position.

In this embodiment the chamber 305 and the grid 321, as components which contact the capsule 307 and the contained powdered substance, are fabricated from a material having a low moisture sensitivity, here a plastics material, such as to reduce any tendency to become tacky in the presence of moisture, and therefore reduce the tendency for the capsule 307 and the powdered substance as contained thereby to adhere to the wall of the chamber 305 or the grid 321.

In this embodiment the rupturing mechanism 309 comprises a piercing element 323, here including two pins, which is operable to pierce the capsule 307, and thereby provide for the release of the contained powdered substance on the generation of a flow through the chamber 305.

In one embodiment the capsule 307 is a gelatine capsule.

In another embodiment the capsule 307 can be manufactured from a material which has a reduced tendency to become tacky in the presence of moisture, as occurs with gelatine capsules, and therefore reduce the tendency for the capsule 307 to adhere to the wall of the chamber 305 or the grid 321.

In one embodiment the capsule 307 is formed of a cellulose derivative, such as hydroxypropyl methylcellulose (HPMC), hydroxypropylcellulose, methylcellulose, ethylcellulose and carboxymethylcellulose In another embodiment the capsule 307 can comprise a plastics material, preferably a water insoluble material, such as a polycarbonate.

In one embodiment the capsule 307 can be manufactured from a lightweight material, such as thin-wall section polymeric materials, which reduces the energy required to move the capsule 307, typically by one or both of vibration and rotation, and thereby allows the delivery device to be operated at reduced flow rates, which is particularly advantageous for nasal delivery.

In one embodiment the capsule 307 has a wall section of less than about 0.25 mm, and more preferably less than about 0.2 mm.

In an alternative embodiment the capsule 307 can include an outer coating of a material which has a reduced tendency to become tacky in the presence of moisture, as occurs with gelatine capsules, and therefore reduce the tendency for the capsule 307 to adhere to the wall of the chamber 305 or the grid 321.

In one embodiment the coated capsule 307 can be formed of gelatine.

In one embodiment the coating can comprise one of parylene, hydroxypropyl methylcellulose (HPMC), hydroxypropylcellulose, methylcellulose, ethylcellulose, carboxymethylcellulose, polyvinyl alcohol, acrylic acid polymer, methacrylic acid polymer, ethyl acrylic acid polymer, cellulose acetate phthalate, polyvinyl acetate phthalate, hydroxypropyl methylcellulose phthalate and hydroxyl methylcellulose acetate succinate, or any combination of layers thereof.

Figure 17:
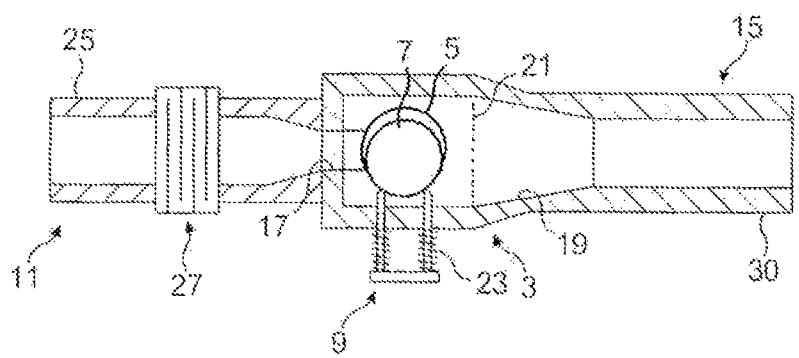

The delivery device of this embodiment is operative to discharge the powdered substance from the capsule 307 by rotation and vibration of the capsule 307, and thus the capsule 307 is preferably formed of a material or coated with a material which exhibits substantially no tackiness in the presence of a moist environment, here a saturated exhaled air flow, that is, does not exhibit an increased moisture content at the outer surface thereof, which would prevent reliable rotation and vibration of the capsule 307.

In this embodiment the capsule 307 is cylindrical in shape, with hemispherical ends.

In other embodiments the capsule 307 could have other geometric forms, such as spherical, which allows for efficient powder release at low flow rates.

In one embodiment the capsule 307 can comprise two or more parts.

In one alternative embodiment the capsule 307 can be constructed to act as the primary environmental barrier for the powdered substance. For instance, the capsule 307 could be constructed from a relatively thick-walled cylindrical section of a polymeric material which includes two metalized thin film closure members which act to seal the ends of the cylindrical section and thus enclose the same.

In this embodiment the gas supply unit 310 comprises a high-pressure reservoir 341, preferably at a pressure of from about 1 bar to about 10 bar, and more preferably at a pressure from about 2 bar to about 10 bar, which, when actuated, delivers a gas flow which acts to drive powder release from the capsule 307. In one embodiment the reservoir 341 can be a pre-filled volume of gas at high-pressure, such as a pressurized canister which contains a propellant. In an alternative embodiment the reservoir 341 can be charged using a pump mechanism.

In this embodiment the gas supply unit 310 is configured such as to be actuated on the generation of a predetermined flow rate through the mouthpiece unit 311, typically a flow rate of from about 10 l/min to about 50 l/min.

In another embodiment the gas supply unit 310 can be configured such as to be actuated on the generation of a predetermined pressure at the mouthpiece unit 311.

In a further embodiment the gas supply unit 310 can be configured such as to be manually actuated.

This configuration is particularly advantageous, in avoiding the use of exhaled air to entrain the powdered substance, and in one embodiment allowing the use of a dry gas. Exhaled air has a high humidity which would lead to condensation both in the chamber 305 and the capsule 307, which can cause problems in the complete entrainment of the powdered substance, both in terms of adhesion of the capsule 307 and the contained powdered substance to the wall of the chamber 305 and adhesion of the powdered substance to the capsule 307, particularly where the powdered substance is a hygroscopic powder.

The mouthpiece unit 311 comprises a mouthpiece 345, in this embodiment as defined by a tubular section, which is gripped in the mouth of the subject.

The nosepiece unit 314 comprises a nosepiece 347, in this embodiment as defined by a tubular section, which is inserted into a nostril of the subject, in this embodiment to provide a sealing fit therewith.

In this embodiment the nosepiece 347, as a component which contacts the powdered substance, is fabricated from a material having a low moisture sensitivity, here a plastics material, such as to reduce any tendency to become tacky in the presence of moisture, and therefore reduce the tendency for the powdered substance to adhere to the wall of the nosepiece 347.

In one embodiment, where the delivery device is a reusable device, the chamber 305, which contains the capsule 307, and the nosepiece 347 comprise a unitary, replaceable component.

Operation of the delivery device will now be described hereinbelow with reference to FIGS. 13 and 14 of the accompanying drawings.

As illustrated in FIG. 13, a subject operates the rupturing mechanism 309 to rupture the capsule 307, inserts the nosepiece 347 into one of his/her nostrils, grips the mouthpiece 345 in his/her mouth, and exhales through the mouthpiece 345.

The exhaled air flow is delivered though the nosepiece 347 into one nasal cavity of the subject.

In this embodiment, as illustrated in FIG. 14, when the exhaled air flow has a predetermined flow rate, the gas supply unit 310 is actuated, such as to deliver a gas flow through the chamber 305. This gas flow acts to move the capsule 307, in this embodiment by vibration and rotation, and entrain the powdered substance as contained by the capsule 307, and the gas flow, as then entraining the powdered substance, is delivered into the exhaled air flow passing through the nosepiece 347 into one nasal cavity of the subject, such that the exhaled air flow entrains the powdered substance into the nasal cavity of the subject. This configuration is particularly advantageous where the gas supply unit 310 is a pressurized canister, as the gas flow from a pressurized canister is cold, and this cold gas is mixed with the warmer exhaled air flow prior to delivery to the nasal cavity.

In this embodiment the exhaled air flow has such a pressure as to pass around the posterior margin of the nasal septum, and into the other nasal cavity, thereby achieving a bi-directional air flow as described in the applicants' earlier WO-A-00/051672.

In one modification, as illustrated in FIG. 15, the gas supply unit 310 could comprise a charged turbine 353, for example, a propeller which is charged by a resilient element, such as spring. With this configuration, on actuation of the gas supply unit 310, stored energy drives the turbine to entrain atmospheric air through the chamber 305 which contains the capsule 307.

Finally, it will be understood that the present invention has been described in its preferred embodiments and can be modified in many different ways without departing from the scope of the invention as defined by the appended claims.

In one embodiment the powdered substance can also be formulated, for example, by coating or blending, such as to reduce the hygroscopicity and transiently increase the dissolution time, and thus reduce any loss of powdered substance in the device due to interaction with condensation on the internal surfaces of the device.

Also, the delivery devices of the described embodiments have been described in relation to the use of capsules 7, 107, 207, 307. It is to be understood that the present invention has application with any kind of powder delivery system, including blisters and metering from bulk, and can be configured as a single-use or multi-use device.

Furthermore, the delivery device of the first-described embodiment could be modified to incorporate a thermoelectric device as the heat exchanger 27, for example, a device which utilizes the Peltier effect, as illustrated in FIG. 16.

In another modification, as illustrated in FIG. 17, the delivery device of the first-described embodiment could be modified such that the chamber 5 is substantially spherical in shape, which is particularly advantageous in allowing for the release of the powdered substance from the capsule 7 in any operative position, and the capsule 7 could be spherical.

The invention claimed is:

1. A nasal delivery device for delivering substance to a nasal cavity of a subject, the delivery device comprising:
   a substance supply unit for supplying a dose of substance to be delivered to the nasal cavity of the subject, the substance supply unit including an inlet and an outlet;
   a nosepiece unit including a nosepiece for fitting to a nasal cavity of the subject and being in fluid communication with the outlet of the substance supply unit; and
   a mouthpiece unit including a mouthpiece in fluid communication with the inlet of the substance supply unit and through which the subject in use exhales such as to entrain substance from the substance supply unit and deliver the same through the nosepiece, and at least one temperature modifier for reducing a temperature of the exhaled air flow such as to reduce the absolute humidity thereof.

2. The delivery device of claim 1, wherein the at least one temperature modifier comprises at least one elongate channel.

3. The delivery device of claim 2, wherein the at least one temperature modifier comprises a plurality of elongate channels.

4. A nasal delivery device for delivering substance to a nasal cavity of a subject, the delivery device comprising:
   a substance supply unit for supplying a dose of substance to be delivered to the nasal cavity of the subject, the substance supply unit including an inlet and an outlet;
   a nosepiece unit including a nosepiece for fitting to a nasal cavity of the subject and being in fluid communication with the outlet of the substance supply unit; and
   a mouthpiece unit including a mouthpiece in fluid communication with the inlet of the substance supply unit and through which the subject in use exhales such as to entrain substance from the substance supply unit and deliver the same through the nosepiece, a plurality of temperature modifiers for reducing a temperature of the exhaled air flow such as to reduce the absolute humidity thereof and which can be fluidly connected successively to the mouthpiece, and a switching mechanism which allows for one of the temperature modifiers to be fluidly connected to the mouthpiece.

5. The delivery device of claim 4, wherein, when the one of the temperature modifiers is fluidly connected to the mouthpiece, the at least one other temperature modifier is vented to atmosphere.

6. The delivery device of claim 4, wherein the switching mechanism comprises a rotatable member to which the temperature modifiers are disposed, whereby rotation of the switching mechanism provides for the one of the temperature modifiers to be in fluid communication with the mouthpiece.

7. The delivery device claim 1, wherein the substance supply unit comprises a container chamber for receiving a substance-containing container which contains a dose of substance.

8. The delivery device of claim 7, wherein the container chamber is substantially cylindrical in shape.

9. The delivery device of claim 7, wherein the container chamber is substantially spherical in shape.

10. A nasal delivery device for delivering substance to a nasal cavity of a subject, the delivery device comprising:
    a substance supply unit operable to supply a dose of substance to be delivered to the nasal cavity of the subject, wherein the substance supply unit comprises a container chamber which includes an inlet and an outlet and contains a substance-containing container which contains a dose of substance;
    a nosepiece unit including a nosepiece for fitting to a nasal cavity of the subject and being in fluid communication with the outlet of the substance supply unit; and
    a mouthpiece unit including a mouthpiece in fluid communication with the inlet of the substance supply unit and through which the subject in use exhales such as to entrain substance from the substance supply unit and deliver the same through the nosepiece;
    wherein the container chamber containing the substance-containing container, and the nosepiece comprise a unitary, replaceable component which is replaced with each operation of the substance supply unit.

11. The delivery device of claim 7, wherein the substance supply unit comprises a rupturing mechanism for rupturing the container as contained in the container chamber.

12. The delivery device of claim 7, wherein the container is formed of a material which exhibits insufficient tackiness in the presence of moisture such as not to adhere to an inner surface of the container chamber during emptying of the container.

13. The delivery device of claim 12, wherein the container is formed of a material which exhibits insufficient tackiness in the presence of moisture in the exhalation air flow for a period of up to about 5 s following exhalation.

14. The delivery device of claim 7, wherein the container is formed substantially of a cellulose derivative.

15. The delivery device of claim 7, wherein the container is formed substantially of gelatine.

16. The delivery device of claim 7, wherein the container is formed of a plastics material.

17. The delivery device of claim 7, wherein the container includes a coating of a material which exhibits insufficient tackiness in the presence of moisture such as not to adhere to an inner surface of the container chamber during emptying of the container.

18. The delivery device of claim 17, wherein the coating is formed of a material which exhibits insufficient tackiness in the presence of moisture in the exhalation air flow for a period of up to about 5 s following exhalation.

19. The delivery device of claim 17, wherein the coating comprises substantially one of parylene, hydroxypropyl methylcellulose (HPMC), hydroxypropylcellulose, methylcellulose, ethylcellulose, carboxymethylcellulose, polyvinyl alcohol, acrylic acid polymer, methacrylic acid polymer, ethyl acrylic acid polymer, cellulose acetate phthalate, polyvinyl acetate phthalate, hydroxypropyl methylcellulose phthalate and hydroxyl methylcellulose acetate succinate, or any combination of layers thereof.

20. The delivery device of claim 17, wherein the container comprises a body of gelatine.

21. The delivery device of claim 7, wherein the container comprises a capsule.

22. The delivery device of claim 21, wherein the capsule is substantially cylindrical in shape.

23. The delivery device of claim 21, wherein the capsule is substantially spherical in shape.

24. The delivery device of claim 1, wherein the at least one temperature modifier is configured to reduce the temperature of the exhaled air flow by more than about 5° C.

25. A nasal delivery device for delivering substance to a nasal cavity of a subject, the delivery device comprising:

a substance supply unit for supplying a dose of substance to be delivered to the nasal cavity of the subject, the substance supply unit including an inlet and an outlet;

a nosepiece unit including a nosepiece for fitting to a nasal cavity of the subject and being in fluid communication with the outlet of the substance supply unit; and a mouthpiece unit including a mouthpiece in fluid communication with the inlet of the substance supply unit and through which the subject in use exhales such as to entrain substance from the substance supply unit and deliver the same through the nosepiece, and at least one temperature modifier for reducing a temperature of the exhaled air flow such as to reduce the absolute humidity thereof, wherein the at least one temperature modifier is configured to allow a flow therethrough at a flow rate of at least about 10 l/min at a pressure of less than about 2 kPa.

26. A nasal delivery device for delivering substance to a nasal cavity of a subject, the delivery device comprising:

a substance supply unit for supplying a dose of substance to be delivered to the nasal cavity of the subject, the substance supply unit including an inlet and an outlet;

a nosepiece unit including a nosepiece for fitting to a nasal cavity of the subject and being in fluid communication with the outlet of the substance supply unit; and a mouthpiece unit including a mouthpiece in fluid communication with the inlet of the substance supply unit and through which the subject in use exhales such as to entrain substance from the substance supply unit and deliver the same through the nosepiece, and at least one temperature modifier for reducing a temperature of the exhaled air flow such as to reduce the absolute humidity thereof;

wherein the at least one temperature modifier is configured such as to provide a pressure drop of not more than about 0.5 kPa to the exhaled air flow.

27. A nasal delivery device for delivering substance to a nasal cavity of a subject, the delivery device comprising:

a substance supply unit for supplying a dose of substance to be delivered to the nasal cavity of the subject, the substance supply unit including an inlet and an outlet;

a nosepiece unit including a nosepiece for fitting to a nasal cavity of the subject and being in fluid communication with the outlet of the substance supply unit; and a mouthpiece unit including a mouthpiece in fluid communication with the inlet of the substance supply unit and through which the subject in use exhales such as to entrain substance from the substance supply unit and deliver the same through the nosepiece, and at least one temperature modifier for reducing a temperature of the exhaled air flow such as to reduce the absolute humidity thereof, wherein the at least one temperature modifier comprises a thermoelectric device.

28. The delivery device of claim 12, wherein the container is formed of a material which exhibits insufficient tackiness in the presence of moisture in the exhalation air flow for a period of up to about 2 s following exhalation.

29. The delivery device of claim 12, wherein the container is formed of a material which exhibits insufficient tackiness in the presence of moisture in the exhalation air flow for a period of up to about 1 s following exhalation.

30. The delivery device of claim 7, wherein the container is formed substantially of one of hydroxypropyl methylcellulose (HPMC), hydroxypropylcellulose, methylcellulose, ethylcellulose and carboxymethylcellulose.

31. The delivery device of claim 17, wherein the coating is formed of a material which exhibits insufficient tackiness in the presence of moisture in the exhalation air flow for a period of up to about 2 s following exhalation.

32. The delivery device of claim 17, wherein the coating is formed of a material which exhibits insufficient tackiness in the presence of moisture in the exhalation air flow for a period of up to about 1 s following exhalation.

33. The delivery device of claim 1, wherein the at least one temperature modifier is configured to reduce the temperature of the exhaled air flow by at least about 12° C.

34. The delivery device of claim 25, wherein the at least one temperature modifier is configured to allow a flow therethrough at a pressure of less than about 1 kPa.

35. The delivery device of claim 25, wherein the at least one temperature modifier is configured to allow a flow therethrough at a flow rate of at least about 20 l/min.

36. The delivery device of claim 25, wherein the at least one temperature modifier is configured to allow a flow therethrough at a flow rate of at least about 30 l/min.

37. The delivery device of claim 25, wherein the at least one temperature modifier is configured to allow a flow therethrough at a flow rate of at least about 40 l/min.

38. The delivery device of claim 25, wherein the at least one temperature modifier is configured to allow a flow therethrough at a flow rate of at least about 50 l/min.

39. The delivery device of claim 1, wherein the at least one temperature modifier is configured such as to provide a pressure drop of not more than about 0.25 kPa to the exhaled air flow.

40. The delivery device of claim 1, wherein the at least one temperature modifier is configured such as to provide a pressure drop of not more than about 0.10 kPa to the exhaled air flow.

41. The delivery device of claim 1, wherein the at least one temperature modifier is configured such as to provide a pressure drop of not more than about 0.05 kPa to the exhaled air flow.

42. The delivery device of claim 1, wherein the at least one temperature modifier is configured such as to provide a pressure drop of not more than about 0.25 kPa to the exhaled air flow.

* * * * *

UNITED STATES PATENT AND TRADEMARK OFFICE
CERTIFICATE OF CORRECTION

PATENT NO. : 8,899,229 B2
APPLICATION NO. : 11/816984
DATED : December 2, 2014
INVENTOR(S) : Per Gisle Djupesland et al.

It is certified that error appears in the above-identified patent and that said Letters Patent is hereby corrected as shown below:

On the title page 2, col. 2, under item (56), line 8, FOREIGN PATENT DOCUMENTS, please correct a typography as follows:
        Delete "JP 53/0848741 7/1978" and replace it with "JP 53084871 7/1978"

On the title page 2, col. 2, under item (56), lines 3 & 6, OTHER PUBLICATIONS, please correct two typographies as follows:
        Delete "U.S. Appl. No. 14/724,636" and replace it with "U.S. Appl. No. 13/724,636"
        Delete "U.S. Appl. No. 13/005,363" and replace it with "U.S. Appl. No. 14/005,363"

Signed and Sealed this
Fifth Day of May, 2015

Michelle K. Lee
*Director of the United States Patent and Trademark Office*